US012758722B2

(12) United States Patent
Foster et al.

(10) Patent No.: US 12,758,722 B2
(45) Date of Patent: Oct. 13, 2026

(54) CHIMNEY SHUTTLING MECHANISM FOR AN INHALER

(71) Applicant: AstraZeneca AB, Södertälje (SE)

(72) Inventors: Brian Foster, Raleigh, NC (US); Dan Deaton, Holly Springs, NC (US); Daniel Cooney, Raleigh, NC (US); James Hannon, Lafayette, CO (US); Eric Richardson, Cave Creek, AZ (US); Paul Hayton, Bristol (GB); Cal McLennan, Chepstow (GB)

(73) Assignee: AstraZeneca AB, Södertälje (SE)

( * ) Notice: Subject to any disclaimer, the term of this patent is extended or adjusted under 35 U.S.C. 154(b) by 351 days.

(21) Appl. No.: 18/666,623

(22) Filed: May 16, 2024

(65) Prior Publication Data

US 2025/0352747 A1 Nov. 20, 2025

(51) Int. Cl.
*A61M 15/00* (2006.01)

(52) U.S. Cl.
CPC ...... *A61M 15/0021* (2014.02); *A61M 15/003* (2014.02); *A61M 15/0086* (2013.01); *A61M 2202/064* (2013.01)

(58) Field of Classification Search
CPC ............. A61M 15/00; A61M 15/0001; A61M 15/0005; A61M 15/0008; A61M 15/0021; A61M 15/0023; A61M 15/0026; A61M 15/0028; A61M 15/003; A61M 15/0033; A61M 15/0038; A61M 15/0041; A61M 15/0061; A61M 15/0086; A61M 2202/064
See application file for complete search history.

(56) References Cited

U.S. PATENT DOCUMENTS

| | | | |
|---|---|---|---|
| 9,339,614 B2 | 5/2016 | Chen et al. | |
| 10,828,432 B1 | 11/2020 | O'Flaherty et al. | |
| 11,213,635 B2 * | 1/2022 | Hepworth | A61M 15/06 |
| 2005/0183723 A1 | 8/2005 | Pinon et al. | |
| 2007/0060868 A1 * | 3/2007 | Tsutsui | A61M 15/004 604/275 |

(Continued)

FOREIGN PATENT DOCUMENTS

| | | |
|---|---|---|
| CN | 213466379 U | 6/2021 |
| CN | 115814218 B | 5/2023 |

(Continued)

OTHER PUBLICATIONS

International Search Report and Written Opinion for International Application No. PCT/IB2025/055017, European Patent Office, Netherlands, mailed on Jul. 28, 2025, 14 pages.

*Primary Examiner* — Colin W Stuart
(74) *Attorney, Agent, or Firm* — Sterne, Kessler, Goldstein & Fox P.L.L.C.

(57) ABSTRACT

An inhaler includes a main body having an inhalation chimney and a mouthpiece. The inhalation chimney includes a bottom surface. The inhaler includes a drawer for receiving a capsule. The drawer includes a top surface. The drawer opens out of and closes into the main body. The drawer moves into the main body from an open position to a closed position or out of the main body from the closed position to the open position, such that the movement of the drawer causes the inhalation chimney to move with respect to the mouthpiece. When the drawer is in the closed position, the top surface of the drawer and the bottom surface of the inhalation chimney are held together.

20 Claims, 11 Drawing Sheets

(56) References Cited

U.S. PATENT DOCUMENTS

| | | | | |
|---|---|---|---|---|
| 2007/0295332 | A1 | 12/2007 | Ziegler et al. | |
| 2011/0120463 | A1* | 5/2011 | Esteve | A61M 15/0035 128/203.15 |
| 2011/0232637 | A1 | 9/2011 | Kaemper et al. | |
| 2013/0016787 | A1 | 1/2013 | Kim et al. | |
| 2013/0047985 | A1 | 2/2013 | Harris et al. | |
| 2015/0059747 | A1* | 3/2015 | Von Schuckmann | A61M 15/0035 128/203.15 |
| 2016/0158470 | A1* | 6/2016 | Esteve | A61M 15/0035 128/203.15 |
| 2018/0043111 | A1* | 2/2018 | Ahern | A61M 15/003 |
| 2020/0093568 | A1 | 3/2020 | Kemeny et al. | |
| 2022/0225669 | A1 | 7/2022 | Hawes et al. | |
| 2022/0409831 | A1* | 12/2022 | Eliahu | A61M 15/0041 |
| 2023/0364362 | A1 | 11/2023 | Trout et al. | |
| 2024/0042147 | A1 | 2/2024 | Di Castri et al. | |

FOREIGN PATENT DOCUMENTS

| | | | | |
|---|---|---|---|---|
| CN | 119345540 | A | 1/2025 | |
| DE | 102007040366 | A1 | 2/2009 | |
| EP | 1270034 | A2 | 1/2003 | |
| GB | 952656 | A | 3/1964 | |
| WO | WO-2007144659 | A1 | 12/2007 | |
| WO | WO-2013016787 | A1 | 2/2013 | |
| WO | WO-2015006838 | A1 | 1/2015 | |
| WO | WO-2015166239 | A1 * | 11/2015 | A61M 15/0028 |
| WO | WO-2017042701 | A1 | 3/2017 | |
| WO | WO-2021083908 | A1 | 5/2021 | |
| WO | WO-2021152488 | A1 | 8/2021 | |
| WO | WO-2022223514 | A1 | 10/2022 | |
| WO | WO-2023038607 | A1 | 3/2023 | |
| WO | WO-2024038236 | A1 | 2/2024 | |

* cited by examiner

CHIMNEY SHUTTLING MECHANISM FOR AN INHALER

FIELD OF DISCLOSURE

The present disclosure relates to inhalers, and more specifically, to chimney shuttling mechanisms for use in dry-powder inhalers.

BACKGROUND

Inhalers are medical devices used to deliver a dose of medicament to a user by inhalation. There are numerous varieties of inhalers, but they all rely on the deliverance of the medicament into a user's lungs where the medicament may then be absorbed. Inhalers are used as a common treatment for asthma and chronic obstructive pulmonary disease (COPD), for example.

Dry powder inhalers are one such variety of inhaler. These deliver medicament to a user in the form of a dry powder, which is advantageous as this allows the medicament to reach further into the lungs than, for instance, metered dose or soft mist inhalers, thereby providing a greater therapeutic benefit to the user.

Existing dry powder inhalers, such as those described in EP 1,270,034 A2 and US 2007/295332 A1, may comprise inhalation chimneys that are built in to the main body such that they cannot move with respect to other components.

Such existing inhalers may face issues such as capsule clashing when the inhaler is opened. If the capsule has shifted into an awkward position, it may clash with the chimney and prevent the inhaler from being successfully opened. A user may therefore be unable to remove the capsule from the inhaler and replace it with a new one, meaning that the inhaler cannot be used. Attempting to remove the capsule by other means could result in damage to the inhaler, which may affect its suitability for providing medicament to the user. Compromises are also made between sealing the inhaler during use and clearances between moving components of the inhaler.

The present disclosure aims to solve these problems, among others.

BRIEF SUMMARY

Aspects of the disclosure are as set out in the independent claims and additional features are set out in the dependent claims. Aspects of the disclosure may be provided in conjunction with each other and features of one aspect may be applied to other aspects.

An aspect of the disclosure provides an inhaler comprising: a main body comprising an inhalation chimney and a mouthpiece, the inhalation chimney comprising a bottom surface; and a drawer for receiving a capsule, the drawer comprising a top surface and configured to open out of and close into the main body; wherein the drawer is arranged such that as it moves into the main body from an open position to a closed position, or out of the main body from the closed position to the open position, the movement of the drawer causes the inhalation chimney to move with respect to the mouthpiece; and wherein when the drawer is in the closed position, the top surface of the drawer and the bottom surface of the inhalation chimney are held together.

Additionally, the inhaler may have a longitudinal axis extending from a top of the inhaler proximate to the mouthpiece, through the inhalation chimney and the drawer, to a bottom of the inhaler, wherein the drawer is positioned below the inhalation chimney with respect to the longitudinal axis, and wherein the inhalation chimney is configured to move along the longitudinal axis with respect to the mouthpiece as the drawer moves between the open position and the closed position.

Additionally, the inhalation chimney may be raised with respect to the mouthpiece when the drawer is in the open position, and wherein a top surface of the inhalation chimney may be level with a top surface of the mouthpiece when the drawer is in the closed position. This means that the surfaces may be level when the inhaler is used, which provides greater comfort for a user.

Additionally, the drawer may comprise at least one guide post and the inhalation chimney comprises at least one protruding rib, the at least one protruding rib comprising a bottom surface facing down towards the bottom of the inhaler with respect to the longitudinal axis, wherein the at least one guide post is configured to slide along the bottom surface of the at least one protruding rib as the drawer moves between the open position and the closed position. This enables the inhalation chimney to move during opening and closing to predetermined levels.

Additionally, moving the drawer out of the main body from the closed position towards the open position may cause the at least one guide post to slide along the bottom surface of the at least one protruding rib, thus causing the inhalation chimney to move upwards. This helps to prevent a capsule from clashing with the inhalation chimney.

Additionally, the protruding rib may comprise a first section and a second section, wherein the first section may be substantially perpendicular to the longitudinal axis and a bottom surface of the first section may be curved in a concave manner.

Additionally, the second section may be angled upwards away from the perpendicular. As this interacts with the guide post during an opening motion of the drawer, this helps to move the inhalation chimney upwards.

Additionally, as the drawer moves into the main body from the open position towards the closed position, the at least one guide post may slide along the bottom surface of the first section; and as the drawer moves out of the main body from the closed position towards the open position, the at least one guide post may slide along the bottom surface of the second section, thus causing the inhalation chimney to move upwards, and may then slide along the bottom surface of the first section.

Additionally, the inhalation chimney may further comprise at least one sealing ramp configured to receive the at least one guide post, the at least one sealing ramp having a top surface facing up towards the top of the inhaler with respect to the longitudinal axis, wherein the at least one guide post is configured to slide along the top surface of the at least one sealing ramp as the drawer moves between the open position and the closed position.

Additionally, moving the drawer into the main body from the open position towards the closed position may cause the at least one guide post to slide along the top surface of the at least one sealing ramp, thus causing the inhalation chimney to move downwards with respect to the longitudinal axis. This helps to bring the inhalation chimney and the drawer closer together and create a chamber for the contents of a capsule to mix with air during inhalation.

Additionally, the inhalation chimney may further comprise at least one drawer retention clip configured to lock on to the at least one guide post when the drawer is in the closed position, thereby creating a retention force configured to hold the drawer in a closed position. This may help to prevent the drawer from opening during inhalation.

Additionally, the drawer may further comprise a front bridge and the inhalation chimney may further comprise a front post, the front post configured to lock on to the front bridge when the drawer is in the closed position. This may also help to prevent the drawer from opening during inhalation.

Additionally, the at least one guide post may comprise two guide posts on opposing sides of the drawer. This may help to ensure that the inhalation chimney moves an equal amount on both sides and helps to keep the inhalation chimney locked in place during inhalation.

Additionally, the at least one protruding rib may comprise two protruding ribs on opposing sides of the inhalation chimney, wherein a first of the two protruding ribs is configured to interact with a first of the two guide posts and a second of the two protruding ribs is configured to interact with a second of the two guide posts.

Additionally, the top surface of the drawer may face up towards the top of the inhaler with respect to the longitudinal axis and may be curved in a convex manner; and the bottom surface of the inhalation chimney may face down towards the bottom of the inhaler with respect to the longitudinal axis and may be curved in a concave manner corresponding to the curve of the top surface of the drawer. This matching of the curvatures may help to enable an effective seal to be formed during inhalation.

Additionally, as the at least one guide post passes over the top surface of the at least one sealing ramp, the inhalation chimney may be pulled towards the drawer.

Additionally, use of the inhaler may create a negative pressure that causes a seal to be formed between the top surface of the drawer and the bottom surface of the inhalation chimney.

Additionally, the drawer may be configured to move upwards with respect to the longitudinal axis when the inhaler is used. This may help to bring the surfaces together and enable a seal to be formed during inhalation.

Additionally, the drawer may be configured to rotate about an axle coupled to the main body, such that the drawer can rotate relative to the main body to move between the open position and the closed position, and wherein the clearance between the drawer and the axle is such that the drawer can move upwards with respect to the longitudinal axis and relative to the main body when the inhaler is used.

Additionally, the at least one guide post may be configured to act as a stop to prevent the drawer from opening beyond a predetermined point.

BRIEF DESCRIPTION OF THE FIGURES

Embodiments of the disclosure will now be described, by way of example only, with reference to the accompanying drawings.

DETAILED DESCRIPTION

Figure 1B:
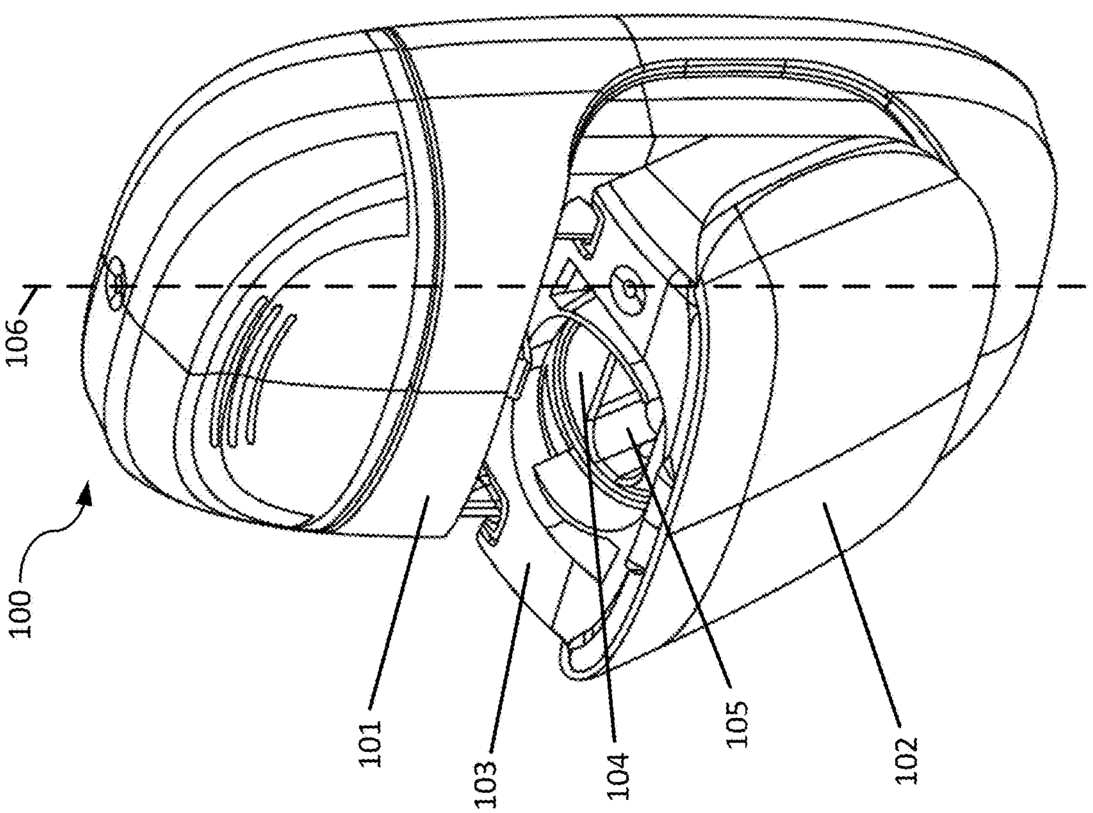
FIG. 1B shows a perspective view of an inhaler with an open drawer in accordance with the present disclosure.
Figure 1A:
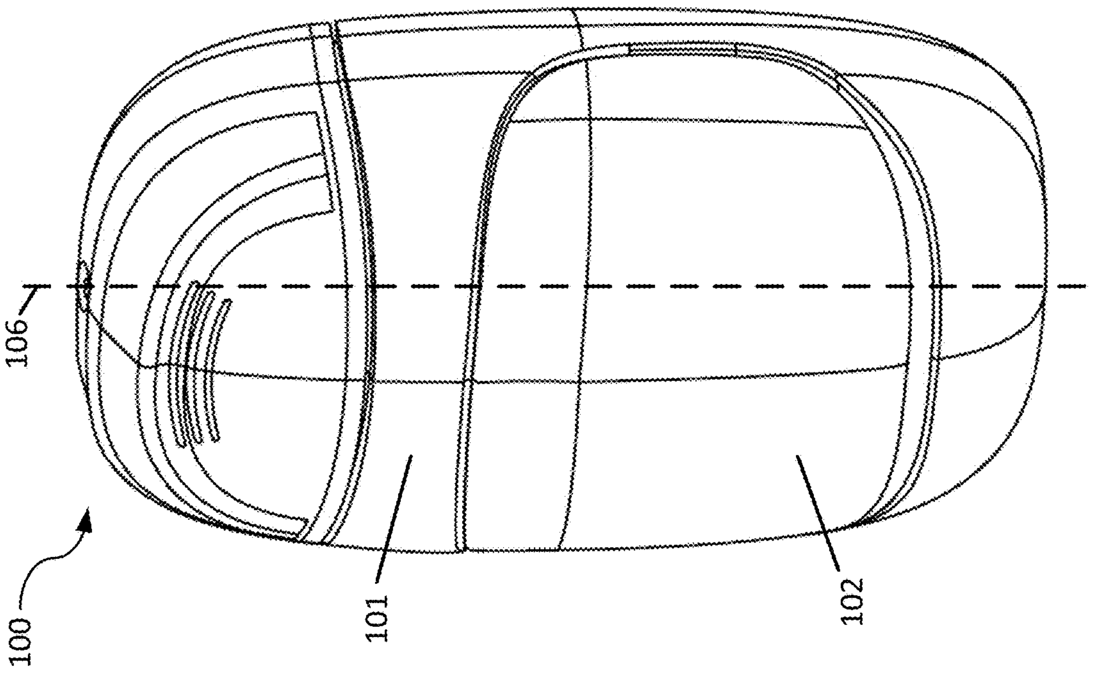
FIG. 1A shows a perspective view of an inhaler in accordance with the present disclosure.

FIGS. 1A-B show perspective views of an inhaler 100. The inhaler 100 comprises a main body 101 and a drawer 102. The drawer 102 may be coupled to the main body by way of a hinge mechanism, which allows the drawer 102 to open out of and close into the main body 101 of the inhaler 100. This enables the drawer 102 to be accessed without having to remove it from the main body 101 entirely. The inhaler 100 may comprise a longitudinal axis 106, with the top of the inhaler 100 being positioned above the bottom of the inhaler 100 with respect to the longitudinal axis 106.

In FIG. 1A, the drawer 102 is shown as being in a closed position. In the closed position, a longitudinal axis of the drawer 102 may directly correspond to the longitudinal axis 106 of the inhaler 100. In FIG. 1B, the drawer 102 is shown as being in an open position, such that the components of the drawer 102 are visible. In the open position, the drawer 102 is angled outwards such that the longitudinal axis of the drawer is angled away from the longitudinal axis 106 of the inhaler 100.

The main body 101 is configured to act as a framework for the inhaler 100 and enclose the majority of the other components of the inhaler 100. The main body 101 may comprise polybutylene terephthalate (PBT) and at least a portion of the main body 101 may comprise wax-lubricated PBT. The main body 101 may comprise at least one air inlet to allow air to flow through the inhaler 100. The drawer 102 is configured to be opened out of and closed into the main body 101. More specifically, the spin chamber 103 of the drawer 102 is configured to receive a capsule and to allow the contents of the capsule to mix with air during inhalation. The contents of the capsule may comprise medicament in the form of a dry powder.

The drawer 102 comprises a spin chamber 103, which is located near the top of the drawer 102 with respect to the longitudinal axis 106. The spin chamber 103 may comprise a primary recess 104 and a secondary recess 105. The primary recess 104 may extend downwards from the top surface of the spin chamber 103. The secondary recess 105 may be located within a bottom surface of the primary recess 104. As such, the secondary recess 105 can be considered as an extension of the primary recess 104. The primary recess 104 may be substantially cylindrical in shape, which may help to encourage rotation of a capsule during inhalation. The secondary recess 105 may be substantially obround in shape, with a length that is greater than its width. The primary recess 104 has a larger volume than the secondary recess 105.

The secondary recess 105 is configured to receive the capsule. The obround shape of the secondary recess 105 enables the capsule to be received horizontally. This may help to ensure that a capsule can be perforated at both ends, thus resulting in a quicker and more efficient release of medication from the capsule. The process of perforation will be described with reference to FIG. 2. The primary recess 104 is configured to allow the contents of the capsule to mix with air during inhalation.

Use of the inhaler 100 begins with the insertion of a capsule into the drawer 102. The capsule is placed into the secondary recess 105 and the drawer 102 is closed into the main body 101. Closing the drawer 102 causes the capsule to be perforated, which will be described in greater detail with respect to FIG. 2. As the user inhales through the mouthpiece (not shown), the air flow through the spin chamber 103 causes the capsule to be lifted out of the secondary recess 105 into the primary recess 104, where it may spin such that its contents may mix with air flowing through the spin chamber 103. This mixture is then inhaled by the user. The drawer 102 may then be opened and the capsule removed.

The inhaler 100 and its use will be described in greater detail with respect to FIG. 2.

Figure 2:
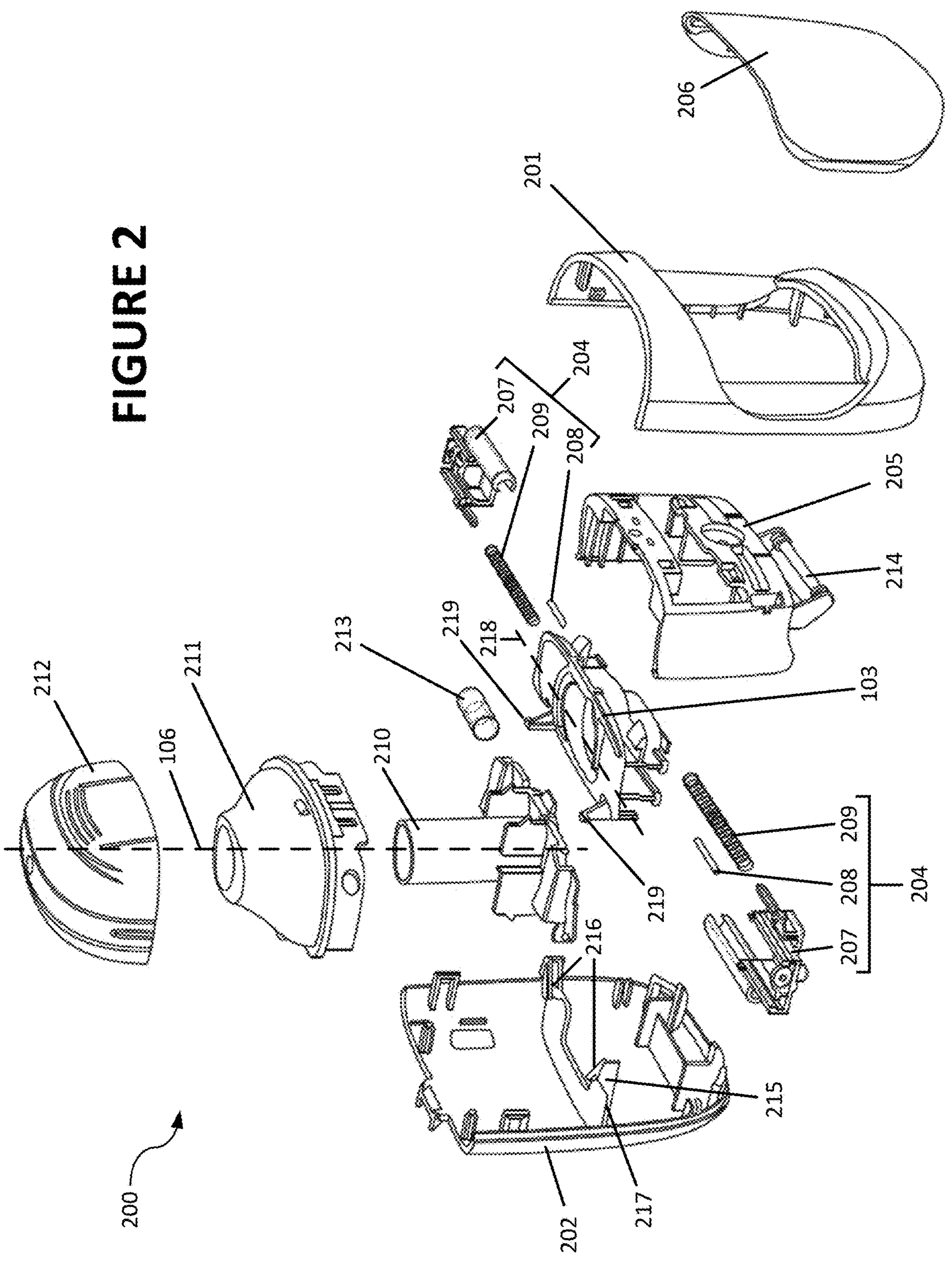
FIG. 2 shows an exploded view of an inhaler in accordance with the present disclosure.

FIG. 2 shows an exploded view of an inhaler 200. The inhaler 200 may correspond to the inhaler 100 from FIGS. 1A-B and may therefore comprise a main body and a drawer, corresponding respectively to the main body 101 and the drawer 102 from FIGS. 1A-B.

More specifically, the main body of inhaler 200 may comprise a front casing 201 and a rear casing 202. The front casing 201 and rear casing 202 are connected to each other to provide a space within which other components of the inhaler 200 may be located. Each of the front casing 201 and rear casing 202 comprises an inner surface and an outer surface. When the front casing 201 and rear casing 202 are connected to each other, the two inner surfaces face inwards towards each other, while both outer surfaces face outwards. The front casing 201 and rear casing 202 both extend upwards along a longitudinal axis that may correspond to the longitudinal axis 106 from FIGS. 1A-B.

The front casing 201 comprises an aperture through which the drawer may move between an open position and a closed position. When the drawer is in the closed position, an outer surface of the drawer casing substantially fills the aperture of the front casing 201. When the drawer is in the open position, the components of the drawer are exposed, such that a capsule 213 may be inserted into or removed from the drawer. As described, the capsule 213 may contain medicament in the form of a dry powder.

The rear casing 202 may comprise at least one wedge 215, the at least one wedge 215 comprising an inner side 216 and being connected to a flexible arm 217. FIG. 2 shows an embodiment in which the rear casing 202 comprises two wedges 215, each comprising an inner side 216 and each attached to a separate flexible arm 217, but it is to be understood that fewer or more wedges 215 and flexible arms 217 are possible. In FIG. 2, the flexible arms 217 protrude outwards from the inner surface of the rear casing 202 along an axis that is substantially perpendicular to the longitudinal axis 106 of the rear casing 202.

The drawer of inhaler 200 may comprise a spin chamber 103, perforating means 204, a supporting framework 205 and a drawer casing 206. The spin chamber 103 may correspond to the spin chamber 103 from FIG. 1B and may comprise a transverse axis 218 that is substantially perpendicular to the longitudinal axis 106 of the inhaler and also substantially perpendicular to the axis along which the flexible arm 217 protrudes. The spin chamber 103, in addition to comprising a primary recess 104 and a secondary recess 105 for receiving a capsule 213, may also comprise at least one guide post 219. FIG. 2 shows an embodiment in which the spin chamber 103 comprises two guide posts 219, each located on opposing sides of the spin chamber 103 along the transverse axis 218. The guide posts 219 may extend upwards from a top surface of the spin chamber 103 substantially along the longitudinal axis 106.

The spin chamber 103 is coupled to the perforating means 204, which are positioned at a side of the spin chamber 103 along the transverse axis 218. The perforating means 204 are positioned so as to be able to move along the transverse axis 218 between a resting position and a perforating position. The perforating position is a position within the secondary recess 105 where the perforating means 204 may perforate the capsule 213. When in the resting position, the perforating means are further away from the centre of the spin chamber 103 than when in the perforating position. The spin chamber 103 may comprise rails to allow the perforating means 204 to slide along the transverse axis 218 between the resting position and the perforating position. The perforating means 204 may comprise grooves that interact with the rails of the spin chamber 103 to enable this movement. The spin chamber 103 may also comprise a T-rail (not shown) that helps to maintain alignment of the spin chamber 103 and the perforating means 204. The spin chamber 103 may further comprise perforating means retention clips (not shown) that prevent the perforating means 204 from moving outwards beyond their resting position along the transverse axis 218.

The spin chamber 103 and perforating means 204 may be coupled to the supporting framework 205, which holds the spin chamber 103 in a set position within the drawer. The supporting framework 205 also encloses the perforating means 204 within the drawer and may also help to prevent the perforating means 204 from moving outwards beyond their resting position along the transverse axis 218. A front side of the supporting framework 205 is attached to the drawer casing 206. The supporting framework may also comprise a hinge 214, which may be connected to the front casing 201 by way of a hook mechanism. The hook mechanism may have a substantially semi-circular cross section. The hinge 214 may also be connected to the rear casing 202. The presence of the hinge 214 may enable the drawer to be opened out of and closed into the main body while remaining attached to the main body. This enables the drawer to be accessed without having to remove it from the main body entirely.

The perforating means 204 may comprise a cam post 207, a needle 208 and a spring 209. The cam post 207 is coupled to a non-perforating end of the needle 208 and to a first end of the spring 209. The needle 208 and spring 209 both extend away from the cam post 207 along the transverse axis 218. The needle 208 may be encompassed by the spring 209, or it may be positioned away from the spring 209.

The second end of the spring 209 may be coupled to an inner portion of the perforating means 204, whereas the perforating end of the needle 208 is not directly connected to any other part of the inhaler. The spring 209 is in a rest state when the drawer is in the open position and when the drawer is in the closed position, but may be compressed as the drawer moves from the open position to the closed position, as will be described in greater detail.

FIG. 2 shows the perforating means 204 as comprising two sets of cam posts 207, needles 208 and springs 209, with each set located along the transverse axis 218 on opposing sides of the spin chamber 103, although the preceding paragraphs have so far described only one cam post 207, one needle 208 and one spring 209. It is to be understood that the inhaler may function with one cam post 207, one needle 208 and one spring 209, or with two cam posts 207, two needles 208 and two springs 209. The only requirements are that the perforating means comprises at least one cam post 207, at least one needle 208 and at least one spring 209. In an embodiment, the perforating means comprises two cam posts 207, two needles 208 and two springs 209, as shown in FIG. 2. In this embodiment, each of the two springs 209 may be coupled to the same inner portion of the perforating means at their respective second ends.

The two needles 208 may comprise a pair of opposing needles 208, each needle 208 coupled to a respective spring 209. The use of two opposing needles 208 may result in two perforations of the capsule 213. This decreases the time required for the contents of the capsule 213 to be removed from the capsule 213 through inhalation, since there will be two holes created in the capsule 213. The opposing needles 208 may be configured to perforate the capsule 213 at the same time. This helps to ensure an efficient and timely emptying of the capsule 213, since both holes will be created at the same time.

As described, the secondary recess 105 may be substantially obround-shaped. The needles 209 may be configured to enter opposing ends of the secondary recess 105 and subsequently perforate opposing ends of the capsule 213. This helps to ensure an efficient and timely emptying of the capsule, since this minimises the distance the contents of the capsule 213 will have to travel in order to exit the capsule 213.

As described, the perforating means 204 are configured to move along the transverse axis 218 between a resting position and a perforating position. More specifically, the cam post may be configured to transversely slide against the bias of the spring 209, which causes the spring 209 to compress. Since the needle 208 is attached to the cam post 207, the needle 208 may also be configured to transversely slide against the bias of the spring 209.

The movement of the drawer from an open position to a closed position may cause the perforating means 204 to move from the resting position to the perforating position.

The inhaler 200 may further comprise an inhalation chimney 210. The inhalation chimney 210 may comprise a hollow tube through which air and medicament may pass. The inhalation chimney 210 is positioned along the longitudinal axis 106 near the top of the inhaler, such that when the drawer is in the closed position, the inhalation chimney is directly above the spin chamber 103. The hollow tube extends along the longitudinal axis 106. The bottom of the hollow tube of the chimney 210 aligns with the primary recess 104 and secondary recess 105 of the spin chamber 103. When the drawer is in the closed position, the inhalation chimney 210 and the spin chamber 103 together define a space within which the contents of the capsule 213 may be spun as air travels through the inhaler 200.

The inhalation chimney 210 may also comprise at least one protruding rib along which the at least one guide post 219 of the spin chamber 103 may pass. The at least one protruding rib may extend outwards along the transverse axis 218. For example, there may be two protruding ribs on opposing sides of the inhalation chimney 210. The number of protruding ribs is the same as the number of guide posts 219.

The inhalation chimney 210 may also comprise at least one drawer retention clip (not shown). The at least one drawer retention clip may be situated near the bottom of the inhalation chimney 210 on the side that is closest to the rear casing 202. In an embodiment, the at least one drawer retention clip comprises two drawer retention clips on opposing sides of the inhalation chimney 210 with respect to the transverse axis 218.

The inhaler 200 may also comprise a mouthpiece 211. The mouthpiece 211 is positioned on top of the inhalation chimney 210 and comprises an aperture through which the inhalation chimney 210 may extend. The inhalation chimney 210 may move upwards along the longitudinal axis 106 such that a top surface of the inhalation chimney 210 is higher than a top surface of the mouthpiece 211 with respect to the longitudinal axis 106. The inhalation chimney 210 may move downwards along the longitudinal axis 106 such that the top surface of the inhalation chimney 210 is at the same level as the top surface of the mouthpiece 211 with respect to the longitudinal axis 106.

The mouthpiece 211 is attached to the front casing 201 and rear casing 202 of the inhaler 200.

The inhaler 200 may also comprise a cap 212. The cap 212 is positioned on top of the mouthpiece 211 and may cover the entire top surface of the mouthpiece 211. The cap 212 is attached to the mouthpiece 211 by way of a hinge mechanism that enables the cap 212 to either allow access to the mouthpiece 211 or to cover and prevent access to the mouthpiece 211.

With reference now to the function of the components of the inhaler 200, the front casing 201 and rear casing 202 are configured to act as the main body of the inhaler 200. The front casing 201 and rear casing 202 are joined to define an outer housing of the inhaler 200, within which other components may be enclosed.

The spin chamber 103, as has been described with reference to FIG. 1B, is configured to receive a capsule 213 and to allow air to mix with the contents of the capsule 213. More specifically, the secondary recess 105 of the spin chamber 103 is configured to receive the capsule 213. As air flows through the inhaler 200, the capsule 213 may be lifted out of the secondary recess 105 and into the primary recess 104, where the capsule 213 may spin around in order to allow its contents to mix with the air.

The perforating means 204 are configured to perforate the capsule 213, thus releasing the contents of the capsule 213 and allowing them to mix with air so that they may be inhaled by a user. More specifically, the perforating means 204 are configured to move inwards along the transverse axis 218 from a resting position to a perforating position as the drawer moves from an open position to a closed position. When at the perforating position, which occurs shortly before the drawer is in the closed position, the perforating means 204 are configured to perforate the capsule 213 and then move back from the perforating position to the resting position. When the drawer is in the closed position, the perforating means 204 are in the resting position. As the drawer moves from the closed position to the open position, the perforating means are configured to remain in the resting position.

The perforating means 204 are configured to interact with a portion of the main body of the inhaler 200 as the drawer moves between the open position and the closed position, which causes the perforating means to move away from their resting position towards their perforating position. More specifically, the perforating means are configured to interact with the wedge 215, which is attached to the flexible arm 217.

As the drawer moves into the main body of the inhaler 200 from the open position to the closed position, the cam post 207 of the perforating means 204 is configured to slide along the inner side 216 of the wedge 215. The angle of this inner side 216 causes the cam post 207 to be pushed inwards towards the centre of the spin chamber 103 along the transverse axis 218, against the biasing of the spring 209. This compresses the spring 209, which subsequently provides a resistive force. This helps to keep the other components of the perforating means 204 in the desired position. The needle 208, which is attached to the cam post 207, also moves inwards towards the centre of the spin chamber 103 and passes through a small aperture in the side of the spin chamber 103. Further details of this small aperture will be discussed with reference to FIGS. 5B-C. By the time the cam post 207 has reached the end of the inner side 216, the perforating means 204 have moved along the transverse axis 218 and have reached their perforating position. When in the perforating position, the needle 208 has extended through the small aperture in the side of the spin chamber 103 and into the secondary recess 105, where it may perforate the capsule 213.

This means that a capsule 213 can be perforated as the drawer is closed into the main body, rather than this being a separate step that must be initiated after the drawer has been closed. This makes use of the inhaler 200 easier and quicker for a user and also minimises the risk of a user failing to perforate a capsule (e.g. by not pressing a button hard enough), since the perforating means 204 must reach the perforating position in order for the drawer to successfully close.

Once the perforating position has been reached and the capsule 213 has been perforated, the perforating means 204 are configured to pass over the edge of the inner side 216 of the wedge 215 and in doing so return to the resting position. The compressed spring 209 decompresses and returns to its rest position. In doing so, the spring 209 pushes the needle 208 out of the secondary recess 105 such that the perforating means 204 can return to the resting position so that they are in the correct position for a subsequent opening of the drawer. At this point, the drawer is in the closed position. Beneficially, this means that a user does not have to manually reset the perforating means 204.

As the drawer is moved from a closed position to an open position, the perforating means 204 are configured to interact with the wedge 215, but in a different manner to the interaction that takes place when the drawer is being closed. As the drawer moves away from the closed position, the perforating means 204 are configured to travel over a top surface of the wedge 215. More specifically, the cam post 207 travels over the top surface of the wedge 215, which causes the flexible arm 217 to move downwards along the longitudinal axis 106 towards the bottom of the inhaler. As the cam post 207 travels over the wedge 215, the perforating means 204 remain in the resting position with respect to the transverse axis 218, meaning that the spring remains in the rest state. Once the cam post 207 has travelled over the top surface of the wedge 215, the wedge 215 moves back up to its normal resting position so that it is in the correct position for a subsequent closing of the drawer.

The inhalation chimney 210 is configured to move downwards with respect to the longitudinal axis 106 as the drawer moves from an open position to a closed position and is configured to move upwards with respect to the longitudinal axis 106 as the drawer moves from a closed position to an open position. More specifically, the guide posts 219 of the spin chamber are configured to interact with the inhalation chimney 210 as the drawer moves between the open and closed positions, which causes the inhalation chimney 210 to move upwards or downwards. When the drawer is in the closed position, the drawer retention clips are configured to hold the guide posts 219 in position, such that a force is required to move the guide posts 219 out of this position and open the drawer.

The mouthpiece 211 is configured to be inserted into a user's mouth during inhalation. The cap 212 is configured to cover the mouthpiece 211 when the inhaler 200 is not in use, thus preventing any foreign substances from entering the inhaler 200 through the mouthpiece 211.

In order to use the inhaler 200, a user may insert a capsule 213 into the secondary recess 105 of the spin chamber 103. The drawer must be in the open position for this to take place, since the spin chamber 103 cannot be accessed if the drawer is in the closed position. Once the capsule 213 is positioned within the secondary recess 105, the user may push the drawer inwards to move it from the open position towards the closed position. As the drawer moves towards the closed position, the perforating means 204 interact with the wedge 215, which causes them to slide along the inner side 216 of the wedge 215 and to move inwards along the transverse axis 218, as has been described.

The movement of the drawer causes the cam post 207 and the needle 208 to move inwards towards the centre of the spin chamber 103 along the transverse axis 218. As the cam post 207 approaches the edge of the wedge 215, the needle 208 perforates the capsule 213. The perforating means 204 then pass over the edge of the wedge 215 and return to the resting position.

The spin chamber 103 also interacts with the inhalation chimney 210 as the drawer moves from the open position towards the closed position. More specifically, the guide posts 219 of the spin chamber 103 slide along the protruding ribs of the inhalation chimney before travelling over sealing ramps of the inhalation chimney 210 as the drawer approaches the closed position. As the guide posts 219 travel over the sealing ramps, they cause the inhalation chimney 210 to be pulled downwards along the longitudinal axis 106, such that a bottom surface of the inhalation chimney 210 is brought closer to a top surface of the spin chamber 103. The two surfaces may be brought into contact, or a small gap may remain between them when the drawer is in the closed position. When the drawer is in the closed position, the inhalation chimney 210 has been pulled down such that a top surface of the inhalation chimney 210 is level with a top surface of the mouthpiece 211 with respect to the longitudinal axis 106. Drawer retention clips hold the guide posts 219 in position, such that the inhalation chimney 210 is held in position with respect to the spin chamber 103.

As discussed above, when the drawer is in the closed position, the perforating means 204 have perforated the capsule 213 and returned to the resting position and the inhalation chimney 210 has moved down towards the spin chamber 103. At this stage, the user may open the cap 212 to expose the mouthpiece 211. By placing the inhaler 200 in their mouth, tilting it and inhaling, an air flow may be generated through the inhaler 200. The air flow may lift the perforated capsule 213 out of the secondary recess 105 and into the primary recess 104 of the spin chamber 103, where it may cause the capsule 213 to spin and the contents of the capsule 213 to mix with the air. The resulting mixture of the contents of the capsule 213 and the air may then pass through the hollow tube of the inhalation chimney 210, through the aperture of the mouthpiece 211 and into the mouth of the user.

Upon successful inhalation, the drawer of the inhaler 200 may then be opened so that the capsule 213 may be removed. As the drawer is pulled outwards, the guide posts 219 push the drawer retention clips away and travel back over the sealing ramps. The guide posts 219 then interact with the protruding ribs of the inhalation chimney 210, which pushes the inhalation chimney 210 upwards with respect to the longitudinal axis 106.

At the same time, the perforating means 204 travel over the wedges 215. This movement pushes the wedges 215 downwards with respect to the longitudinal axis 106. The perforating means 204 therefore remain in the resting position as they travel over the wedges 215.

Figure 3A:
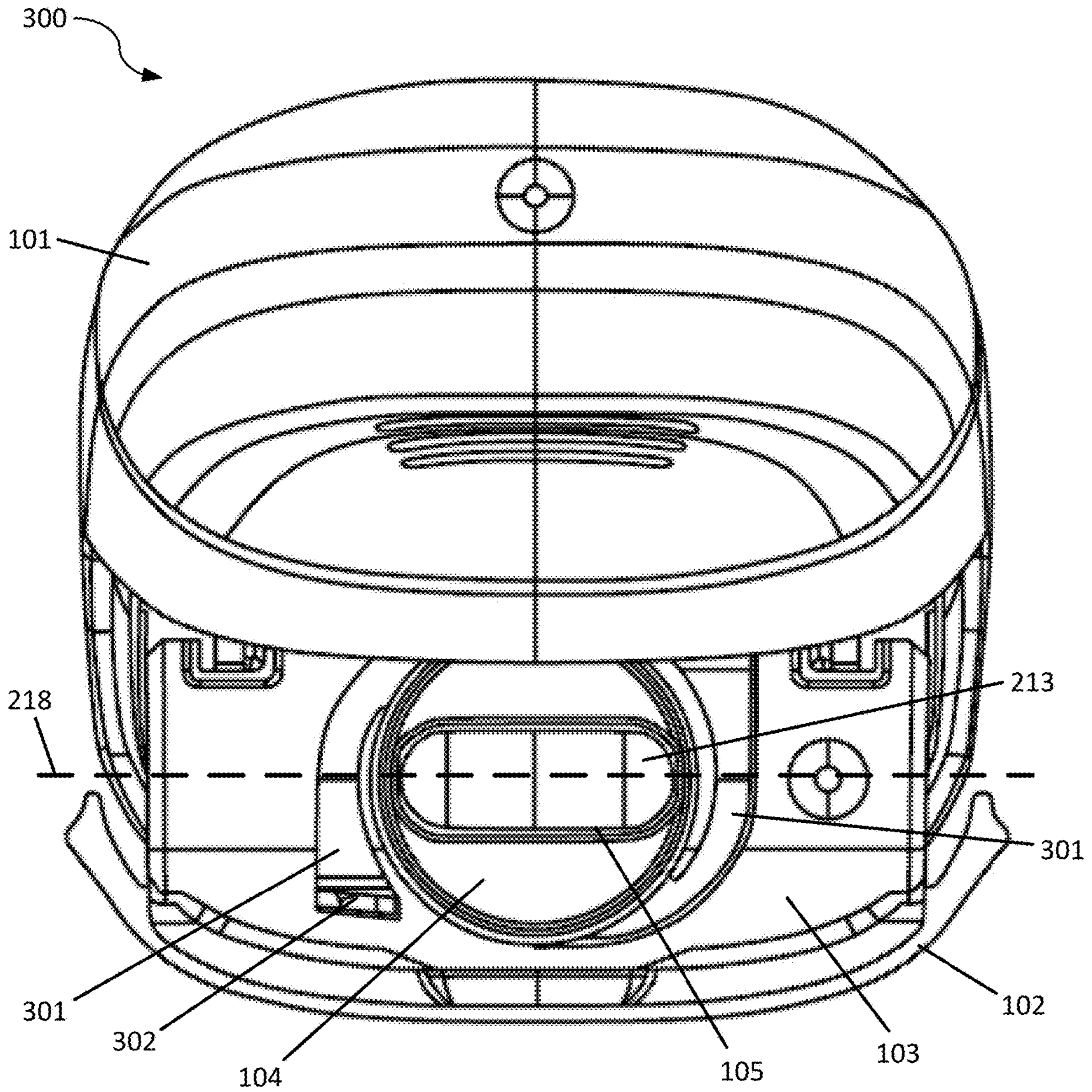
FIG. 3A shows a top view of an inhaler with an open drawer in accordance with the present disclosure.
Figure 3B:
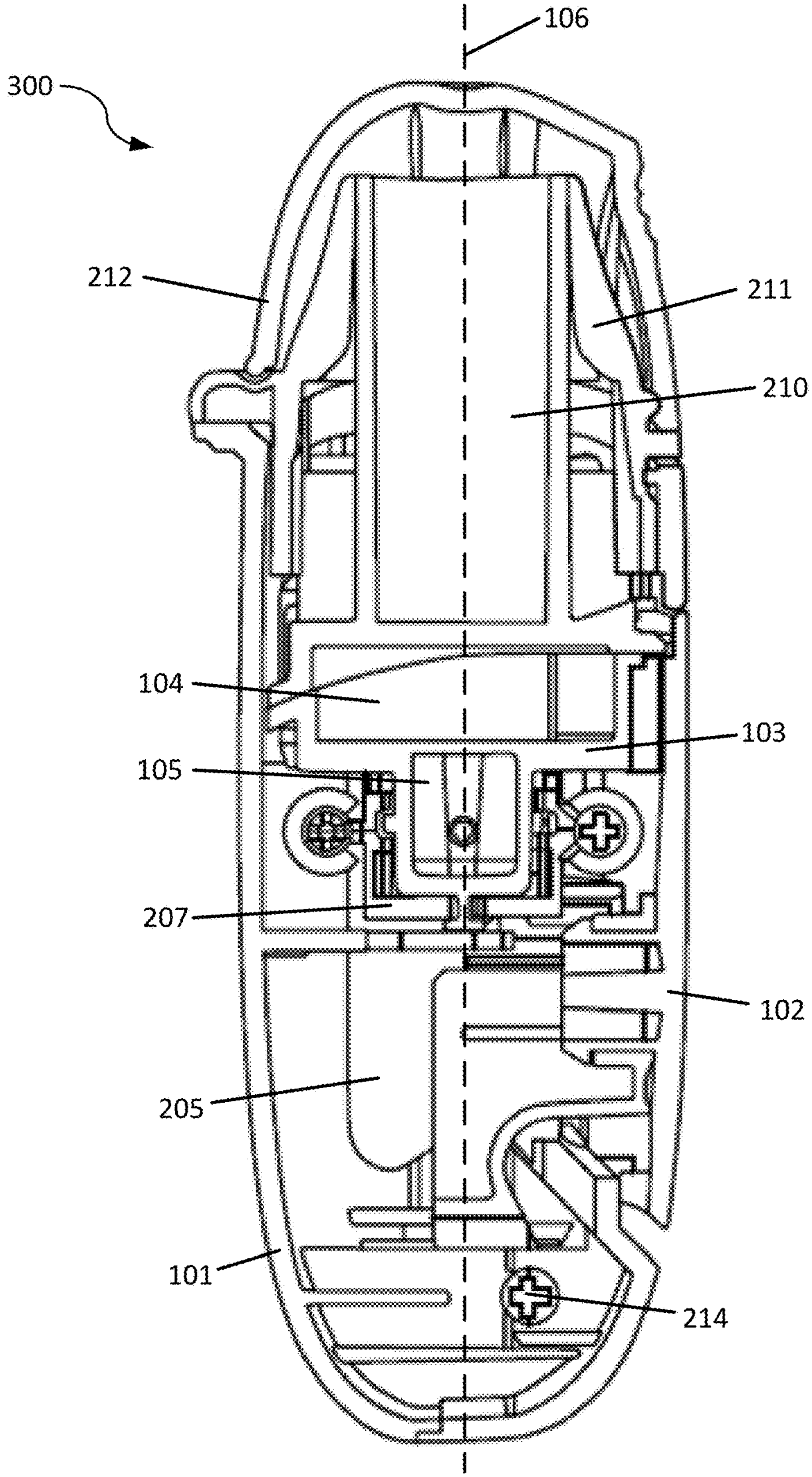
FIG. 3B shows a cross-sectional side view of an inhaler in accordance with the present disclosure.

FIG. 3A shows a top view of an inhaler 300 with an open drawer in accordance with the present disclosure. FIG. 3B shows a cross-sectional side view of an inhaler 300 in accordance with the present disclosure. The inhaler 300 may be the same as the inhaler 100 from FIG. 1 and the inhaler 200 from FIG. 2.

Referring firstly to FIG. 3A, the spin chamber 103 is shown in greater detail. As has been discussed, the spin chamber 103 comprises a primary recess 104 and a secondary recess 105. The secondary recess 105 is configured to receive the capsule 213.

The spin chamber 103 may also comprise at least one curved channel 301, through which air may travel from at least one air inlet 302 into the primary recess 104. The air may then mix with the contents of the capsule 213 during inhalation. FIG. 3A shows an embodiment in which the spin chamber 103 comprises two curved channels 301. The curved channels 301 may be separated from the primary recess 104 along a majority of their length by a curved wall.

Referring now to FIG. 3B, the internal structure of the inhaler 300 when in the closed position is shown. As has been described with reference to FIG. 2, the components of the drawer 102 are enclosed within the main body 101 when the drawer 102 is in the closed position. The inhalation chimney 210 may extend through the mouthpiece 211, which itself is covered by the cap 212. The spin chamber 103 is positioned at the top of the drawer 102, such that when the drawer 102 is in the closed position, the spin chamber 103 is directly underneath the inhalation chimney 210 with respect to the longitudinal axis 106. The spin chamber 103 is coupled to the supporting framework 205, which is attached to the main body 101 by way of a hinge mechanism 214. The cam post 207 is coupled to the side of the spin chamber 103 and is able to move inwards with respect to the transverse axis, but not upwards or downwards with respect to the longitudinal axis 106.

Referring now to both FIGS. 3A and 3B, as has been described, when the drawer 102 is closed into the main body 101 from an open position towards a closed position, the perforating means are configured to interact with a portion of the main body 101, which causes the perforating means to move from a resting position to a perforating position, where the perforating means may perforate a capsule held in the secondary recess 105. As the drawer 102 continues to move towards the closed position, the perforating means return to the resting position and the inhalation chimney 210 is pulled downwards with respect to the longitudinal axis 106, such that a chamber may be defined. As will be described with reference to FIG. 8, this chamber may comprise the primary recess 104, the secondary recess 105 and a volume defined by the inhalation chimney 210. During inhalation, air may travel through the air inlets 302, along the curved channels 301 and into the primary recess 104, into which the capsule 213 has been lifted and the contents of the capsule have begun to empty. The air may then mix with the contents of the capsule 213 as the capsule 213 is spun around by the air.

Figure 4A:
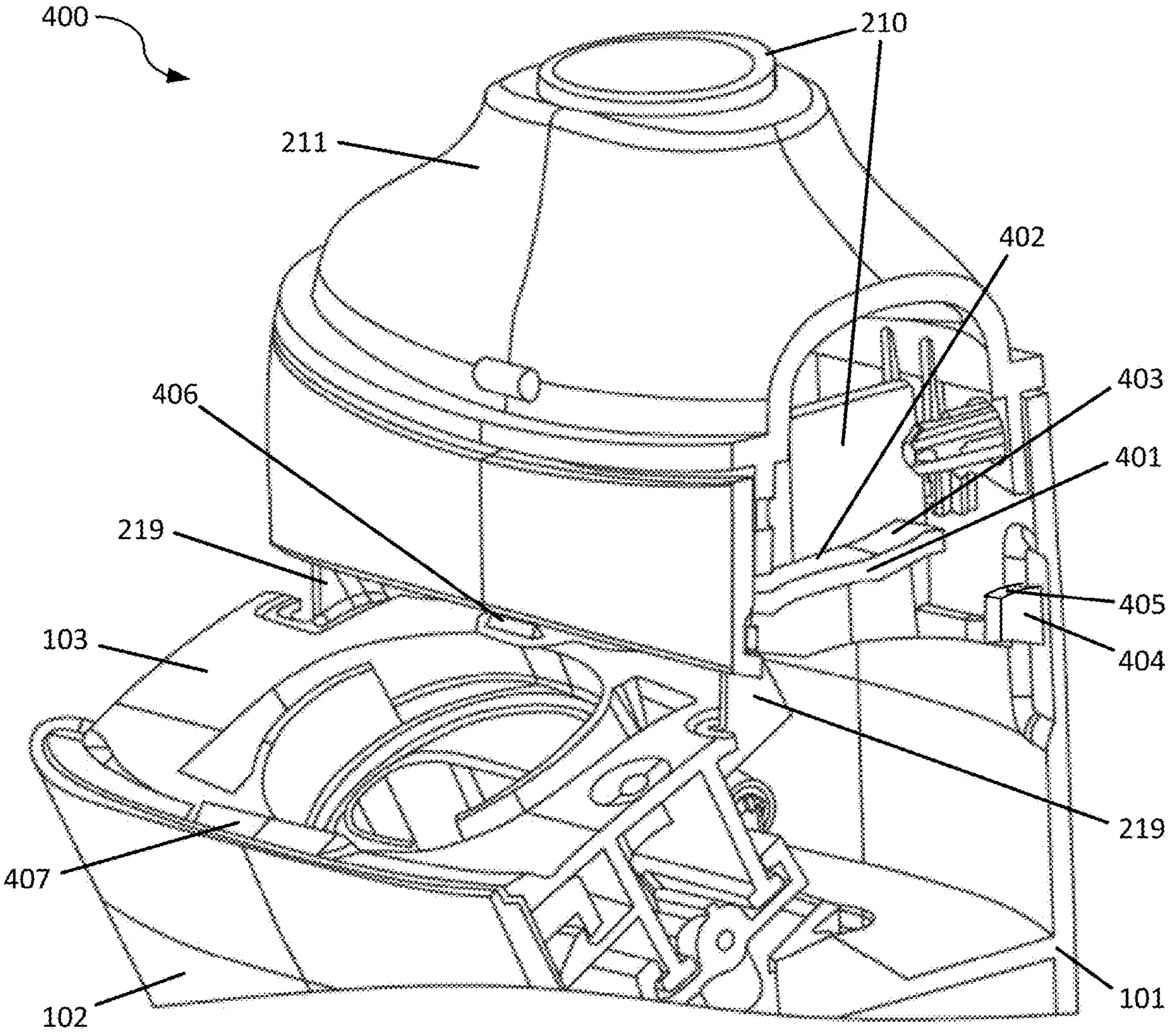
FIG. 4A shows a cross-sectional perspective view of a chimney shuttling mechanism of an inhaler when the drawer is in an open position in accordance with the present disclosure.
Figure 4B:
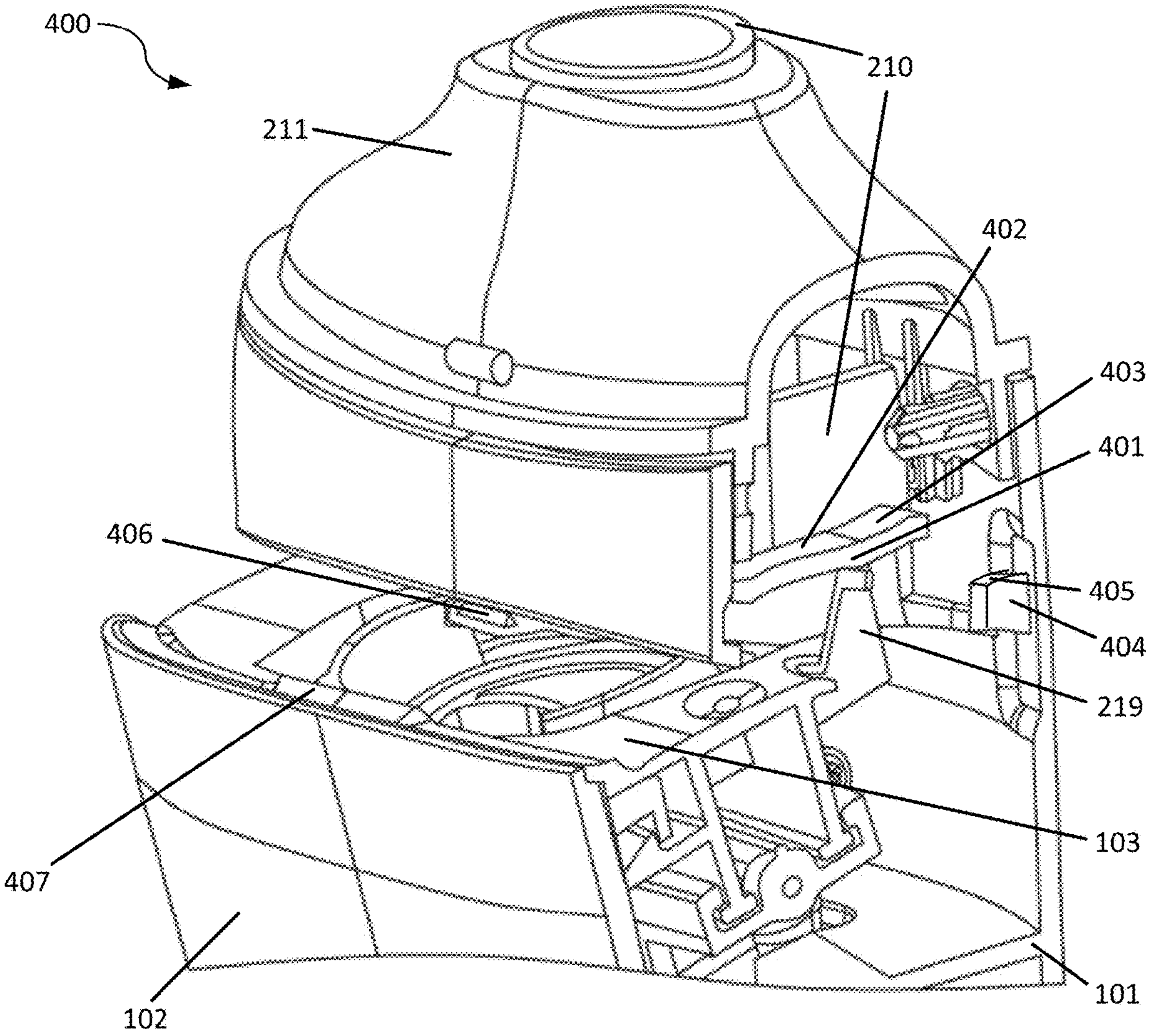
FIG. 4B shows a cross-sectional perspective view of a chimney shuttling mechanism of an inhaler when the drawer is moving from an open position to a closed position in accordance with the present disclosure.
Figure 4C:
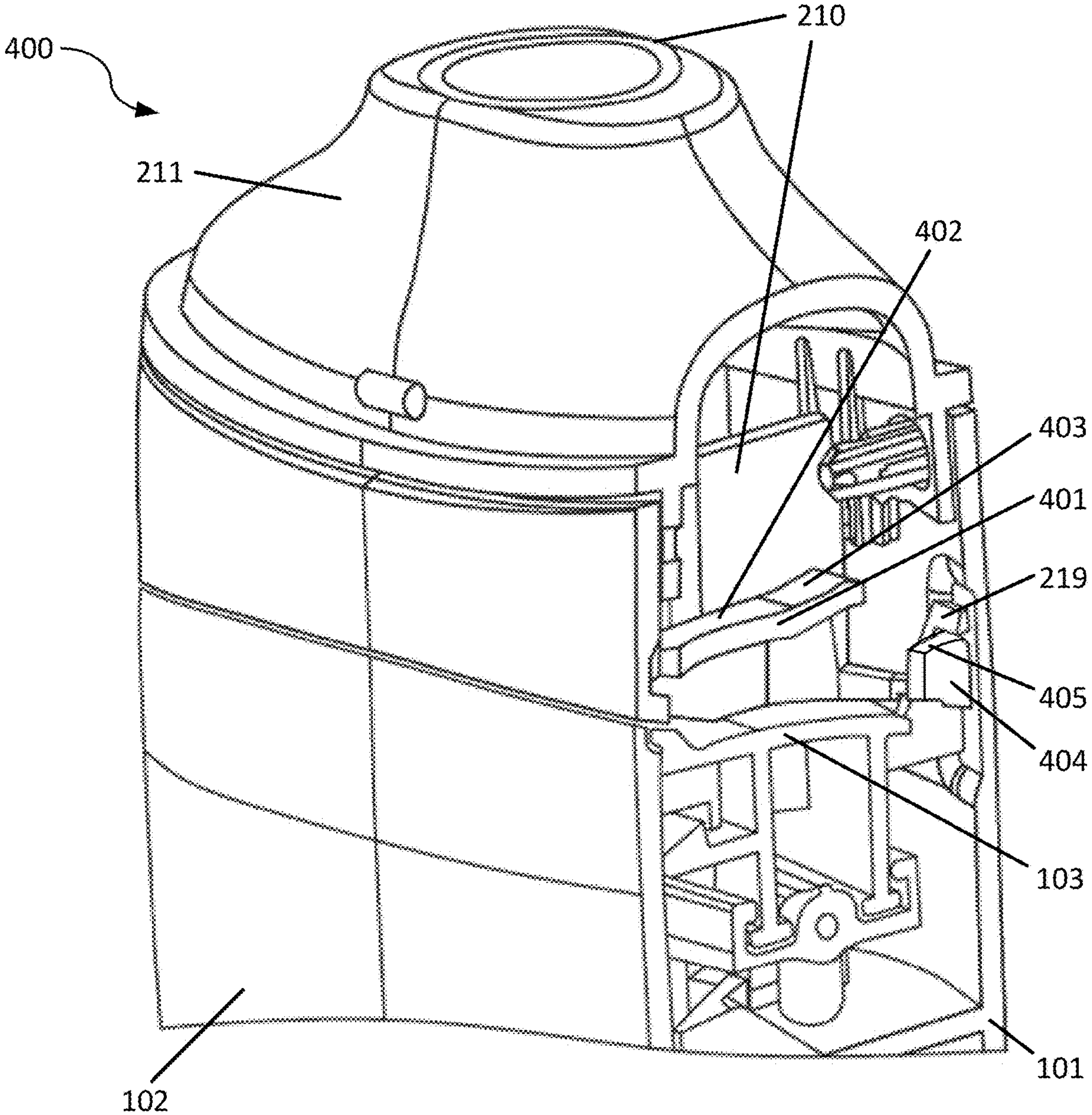
FIG. 4C shows a cross-sectional perspective view of a chimney shuttling mechanism of an inhaler when the drawer is in a closed position in accordance with the present disclosure.

FIGS. 4A-C show cross-sectional perspective views of a chimney shuttling mechanism of an inhaler 400 as the drawer 102 of the inhaler 400 is being closed into the main body 101 of the inhaler 400. The inhaler 400 may directly correspond to inhalers 100, 200 or 300 from the previous Figures.

Specifically, FIG. 4A shows a cross-sectional perspective view of the chimney shuttling mechanism of the inhaler 400 when the drawer 102 is in an open position, FIG. 4B shows a cross-sectional perspective view of the chimney shuttling mechanism of the inhaler 400 when the drawer 102 is being moved from the open position towards a closed position, and FIG. 4C shows a cross-sectional perspective view of the chimney shuttling mechanism of the inhaler 400 when the drawer 102 is in the closed position.

As has been described with reference to the previous Figures, the inhaler 400 may comprise a drawer 102 configured to open out of and close into a main body 101. The drawer 102 may comprise a spin chamber 103, which may comprise at least one guide post 219. FIG. 4A shows an embodiment in which the spin chamber 103 comprises two guide posts 219 each located on opposing sides of the spin chamber 103 along the transverse axis 218. The guide posts 219 may extend upwards from a top surface of the spin chamber 103 substantially along the longitudinal axis 106. In FIGS. 4B and 4C, only one of the two guide posts 219 is visible.

The inhaler 400 may also comprise an inhalation chimney 210, as described with reference to FIG. 2. The inhalation chimney 210 may comprise at least one protruding rib 401. The at least one protruding rib 401 may protrude outwards from a side of the inhalation chimney 210 along the transverse axis 218. In an embodiment, the at least one protruding rib 401 comprises two protruding ribs 401 on opposing sides of the inhalation chimney 210, such that each protruding rib 401 protrudes outwards in an opposite direction to the other protruding rib 401 with respect to the transverse axis 218. A first The at least one protruding rib 401 may comprise a bottom surface facing down towards the bottom of the inhaler 400 with respect to the longitudinal axis 106. The at least one protruding rib 401 may also comprise a first section 402 and a second section 403. The first section 402 may extend from a first end of the protruding rib 401 to a particular point along the length of the protruding rib 401. The second section 403 may extend from this point to a second end of the protruding rib 401. The first section 402 may have a length that is greater than the length of the second section 403, such that the point that marks the boundary between the first section 402 and the second section 403 is closer to the second end of the protruding rib 401 than the first end of the protruding rib 401.

The first section 402 may be substantially perpendicular to the longitudinal axis 106. The bottom surface of the first section 402 of the protruding rib 401 may be curved in a concave manner. This slight curvature may match a curvature of the top surface of the spin chamber 103—this will be described in greater detail with respect to FIGS. 5A-B. Alternatively, the first section 402 may be substantially flat.

The second section 403 may be angled upwards with respect to the perpendicular. The bottom surface of the protruding rib 401 in the second section 403 may therefore also be angled upwards with respect to the perpendicular. Alternatively, the second section 403 may have a substantially identical profile to the first section 402, such that the bottom surface of the protruding rib 401 comprises a single consistent curve. Such an embodiment will be described with reference to FIGS. 5A-B.

The inhalation chimney 210 may also comprise at least one sealing ramp 404. In an embodiment, the inhalation chimney 210 may comprise two sealing ramps 404, thus matching the number of guide posts 219 and protruding ribs 401. The sealing ramps 404 may be block elements located on opposing ends of the inhalation chimney 210 proximate to the rear casing of the main body 101 of the inhaler 400. Each sealing ramp 404 may comprise a top surface 405 that faces substantially upwards with respect to the longitudinal axis 106. The top surface 405 of the sealing ramp 404 may be curved in a convex manner, such that the top surface rises and then falls with respect to the longitudinal axis 106 with distance along its length. In this way, the top surface 405 can be said to comprise a peak in the middle of the top surface 405. This curvature can be seen more clearly in FIGS. 5A-B.

The aforementioned features may together form a chimney shuttling mechanism that enables movement of the inhalation chimney 210. This will be described in greater detail later on.

The inhalation chimney 210 may also comprise a front post 406 extending outwards from a surface of the inhalation chimney 210 that is proximate to the front casing of the main body 101 of the inhaler 400. The front post 406 may be a part of a locking mechanism of the inhaler 400. The drawer 102 may comprise a front bridge 407 that may be part of the same locking mechanism as the front post 406. The front bridge 407 may be located on a top surface of the spin chamber 103 of the drawer 102 and may extend upwards with respect to the longitudinal axis 106. The front bridge 407 may be positioned along a side of the top surface of the spin chamber 103.

As has been described with reference to FIG. 2, the inhaler 400 may also comprise a mouthpiece 211.

The inhaler 400 is arranged such that as the drawer 102 moves into the main body 101 from an open position to a closed position, or out of the main body 101 from the closed position to the open position, the movement of the drawer 102 causes the inhalation chimney 210 to move with respect to the mouthpiece 211.

More specifically, the inhaler is arranged such that the guide posts 219 are configured to interact with the protruding ribs 401 and the sealing ramps 404 as the drawer 102 is moved between the open and closed positions, which causes the inhalation chimney 210 to move with respect to the mouthpiece 211. A first of the two protruding ribs 401 may be configured to interact with a first of the two guide posts 219 and a second of the two protruding ribs 401 may be configured to interact with a second of the two guide posts 219. The sealing ramps 404 are configured to receive the guide posts 219 and hold them in place when the drawer 102 is in the closed position, thus helping to prevent the drawer 102 from opening during inhalation.

Each guide post 219 is configured to slide along the bottom surface of its respective protruding rib 401 and to slide along the top surface 405 of its respective sealing ramp 404, which causes the movement of the inhalation chimney 210. This process will be described in greater detail in the following paragraphs.

The front bridge 407 is configured to lock onto the front post 406 when the inhaler is in the closed position, thus helping to keep the components of the inhaler aligned and sealed during inhalation.

A closing motion of the drawer 102, in which the drawer 102 moves from an open position to a closed position, will now be described.

Referring firstly to FIG. 4A, the inhaler 400 is shown to be in an open position. This means that the spin chamber 103 is fully accessible for removing and/or inserting a capsule. In this open position, the inhalation chimney 210 is at its highest position with respect to the longitudinal axis 106. At this position, a top surface of the inhalation chimney 210 is raised with respect to the mouthpiece 211. This can be seen in FIG. 4A, where the inhalation chimney 210 clearly extends above the mouthpiece 211.

With continued reference to FIG. 4A, each guide post 219 may be in contact with an end of its respective protruding rib 401. The guide posts 219 may also contact the front casing of the main body 101 of the inhaler 400 at this point. Specifically, the contact of the guide posts 219 with the front casing may help to prevent the drawer 102 from opening any further out of the main body 101. In doing so, the guide posts 219 may be configured to act as stops to prevent the drawer 102 from opening beyond a predetermined point. The open position can therefore be defined as the point at which the guide posts 219 are in contact with the front casing of the main body 101 of the inhaler 400. In this position, the front post 406 and the front bridge 407 are not in contact with each other.

Moving now to FIG. 4B, the inhaler 400 is shown to be in a position where the drawer 102 is in between the open position and the closed position. Here, FIG. 4B will be described as an intermediate step of a closing motion of the drawer 102 into the main body 101, but it should be understood that FIG. 4B can also be described as an intermediate step of an opening motion of the drawer 102 out of the main body 101—indeed, this will be described later on.

As the drawer 102 moves towards the closed position, each guide post 219 slides along the bottom surface of its respective protruding rib 401. Specifically, each guide post 219 slides along the bottom surface of the first section 402 of its respective protruding rib 401. At this stage, the inhalation chimney 210 is still in substantially the same position with respect to the mouthpiece 211. As the guide posts 219 reach the second sections 403 of the protruding ribs 401, the angle of the second sections 403 results in a gap forming between the guide posts 219 and the protruding ribs 401, meaning that the guide posts 219 are no longer in contact with the protruding ribs 401.

After the guide posts 219 have interacted with the protruding ribs 401, but before the drawer 102 reaches the closed position, the guide posts 219 interact with the sealing ramps 404. More specifically, each guide post 219 may slide along the top surface 405 of its respective sealing ramp 404 as the drawer 102 moves towards the closed position. As has been described above, the top surface 405 of each sealing ramp 404 is curved in a convex manner such that it comprises a peak. The section of the top surface 405 that first interacts with the guide post 219 during the closing motion is therefore angled upwards with respect to the guide post 219. The guide post 219 therefore pushes the sealing ramp 404 downwards as it slides along the top surface 405 of the sealing ramp 404, which causes the entire inhalation chimney 210 to move downwards with respect to the longitudinal axis 106.

Moving now to FIG. 4C, the inhaler 400 is shown to be in the closed position. This means that the spin chamber 103 is enclosed within the main body 101 of the inhaler 400, and any capsule present within the spin chamber 103 has been perforated.

As has been described, each guide post 219 pushes its respective sealing ramp 404 downwards with respect to the longitudinal axis 106 as it slides along the top surface 405 of the sealing ramp 404. As this happens, the guide post 219 passes over the peak of the top surface 405 and eventually comes to a final position along the top surface 405, at which point the drawer 102 is in the closed position, as shown in FIG. 4C. The guide post 219 may be held in this final position by a drawer retention clip, as will be described in more detail with respect to FIGS. 7A-C.

In the closed position, the inhalation chimney 210 is at its lowest position with respect to the longitudinal axis 106. At this position, the top surface of the inhalation chimney 210 is level with a top surface of the mouthpiece 211. This can be seen in FIG. 4C, where the top surfaces of the inhalation chimney 210 and the mouthpiece 211 are at the same level with respect to the longitudinal axis 106. The inhalation chimney 210 has been pulled downwards towards the drawer 102, and specifically towards the spin chamber 103. A bottom surface of the inhalation chimney 210 may be brought into contact with a top surface of the spin chamber 103, or a small gap may remain between the two surfaces when the drawer is in the closed position.

In the closed position, the front post 406 locks on to the front bridge 407, thus helping to keep the drawer 102 in the closed position.

An opening motion of the drawer 102, in which the drawer 102 moves from a closed position to an open position, will now be described.

Referring firstly to FIG. 4C, the inhaler 400 is shown to be in the closed position. The relative positions of the relevant components of the inhaler 400 in the closed position have already been described with reference to the closing motion of the drawer 102.

As the drawer 102 moves away from the closed position, the front post 406 may unlock from the front bridge 407. Simultaneously, the guide posts 219 may be released by the drawer retention clips and may slide along the top surfaces 405 of their respective sealing ramps 404. The inhalation chimney 210 may move slightly with respect to the longitudinal axis 106 as the guide posts 219 slide along the top surfaces 405 of the sealing ramps 404.

The guide posts 219 move away from the sealing ramps 404 as the drawer 102 is moved further away from the closed position. Eventually, each guide post 219 comes into contact with its respective protruding rib 401 and interacts with said protruding rib 401. More specifically, since the inhalation chimney 210 is still substantially level with the mouthpiece 211 at this stage (in other words, still substantially at its lowest point with respect to the longitudinal axis 106), the second section 403 of each protruding rib 401 is in line with the trajectory of its respective guide post 219. Each guide post 219 therefore firstly interacts with the second section 403 of its respective protruding rib 401. Since the second section 403 is angled upwards with respect to the perpendicular, the guide post 219 slides along the bottom surface of the second section 403 of the protruding rib 401 and therefore pushes the protruding rib 401 upwards as it slides along the bottom surface of the protruding rib 401, which causes the entire inhalation chimney 210 to move upwards with respect to the longitudinal axis 106. The majority of the upwards motion of the inhalation chimney 210 is caused by this interaction between the guide post 219 and the second section 403 of the protruding rib 401.

Moving now to FIG. 4B, the inhaler 400 is shown to be in a position where the drawer 102 is in between the closed position and the open position. Here, FIG. 4B will be described as an intermediate step of an opening motion of the drawer 102 out of the main body 101, but it should be understood that FIG. 4B can also be described as an intermediate step of a closing motion of the drawer 102 into the main body 101, as has already been described.

In FIG. 4B, each guide post 219 has interacted with the second section 403 of its respective protruding rib 401 and is now interacting with the first section 402 of its respective protruding rib 401. More specifically, each guide post 219 may slide along the bottom surface of the first section 402 of its respective protruding rib 401. FIG. 4B shows each guide post 219 interacting with its respective protruding rib 401 in this way.

While the guide posts 219 slide along the bottom surfaces of the first sections 402 of the protruding ribs 401, the inhalation chimney 210 may remain at substantially the same level with respect to the longitudinal axis 106 and with respect to the mouthpiece 211. Depending on the exact curvature and/or angle of the first section 402 of the protruding rib 401, the inhalation chimney 210 may alternatively continue to move upwards with respect to the longitudinal axis 106 as the guide post 219 slides along the bottom surface of the first section 402 of the protruding rib 401 towards the open position.

Referring now to FIG. 4A, the inhaler 400 is shown to be in the open position. This means that the spin chamber 103 is fully accessible for removing and/or inserting a capsule. In this open position, the inhalation chimney 210 is at its highest position with respect to the longitudinal axis 106. At this position, a top surface of the inhalation chimney 210 is raised with respect to the mouthpiece 211. This can be seen in FIG. 4A, where the inhalation chimney 210 clearly extends above the mouthpiece 211.

With continued reference to FIG. 4A, the guide posts 219 are not in contact with the protruding ribs 401 or the sealing ramps 404. The guide posts 219 are in contact with the front casing of the main body 101 of the inhaler 400. Specifically, the contact of the guide posts 219 with the front casing prevents the drawer 102 from opening any further out of the main body 101. The open position can therefore be defined as the point at which the guide posts 219 are in contact with the front casing of the main body 101 of the inhaler 400. In this position, the front post 406 and the front bridge 407 are not in contact with each other.

The upwards motion of the inhalation chimney 210 during movement of the drawer 102 from the closed position to the open position helps to prevent the capsule from clashing with the inhalation chimney 210.

Figure 5A:
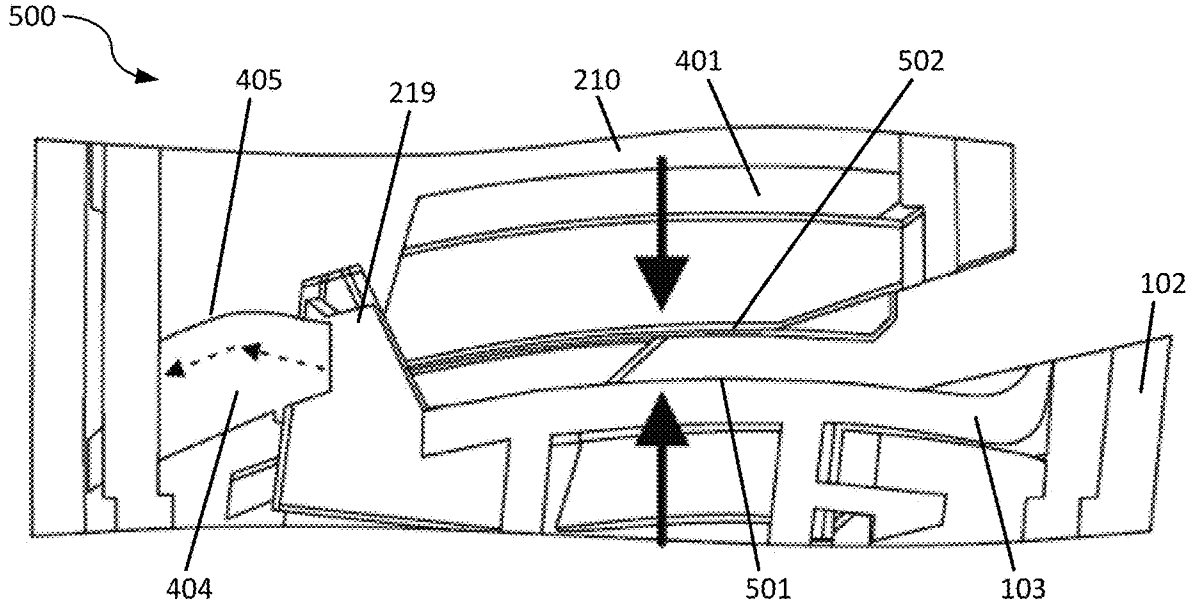
FIG. 5A shows a side view of a chimney shuttling mechanism of an inhaler when the drawer is moving from an open position to a closed position in accordance with the present disclosure.
Figure 5B:
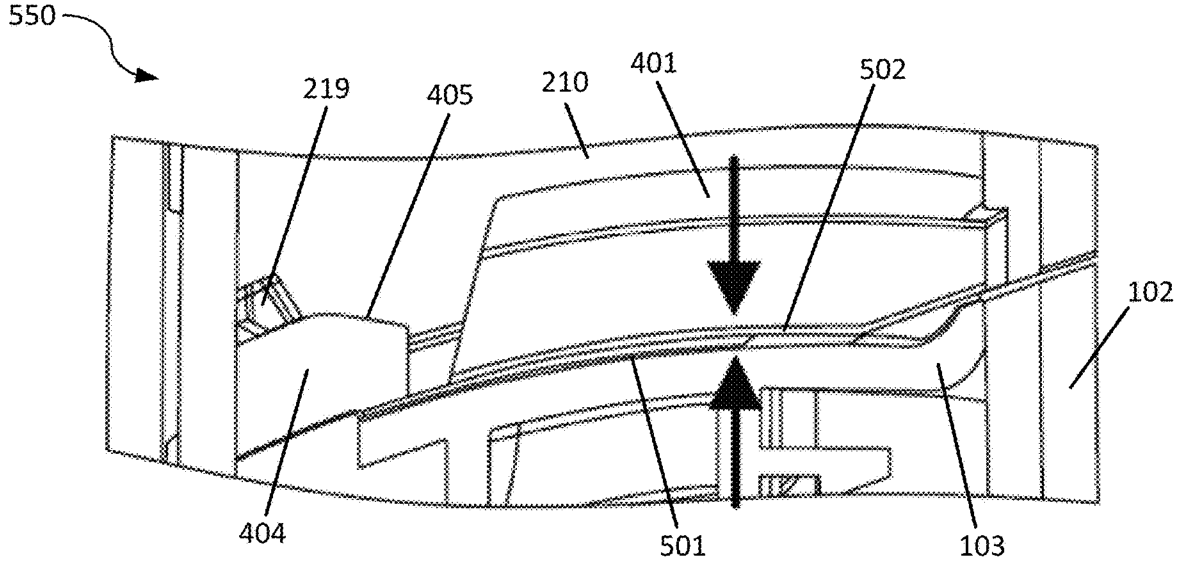
FIG. 5B shows a side view of a chimney shuttling mechanism of an inhaler when the drawer is in a closed position in accordance with the present disclosure.

FIGS. 5A-B show side views of a chimney shuttling mechanism, such as the chimney shuttling mechanism described above with reference to FIGS. 4A-C.

More specifically, FIG. 5A shows a first side view 500 of a chimney shuttling mechanism of an inhaler when the drawer 102 is moving from an open position to a closed position. FIG. 5B shows a second side view 550 of the same chimney shuttling mechanism when the drawer 102 is in the closed position. The inhaler may be the same as inhalers 100, 200, 300 or 400 from the previous Figures.

The features of the chimney shuttling mechanism have already been described with reference to FIGS. 4A-C. Additionally, it should be noted that the drawer 102 may comprise a top surface 501 (which may also be considered as a top surface of the spin chamber 103) and the inhalation chimney 210 may comprise a bottom surface 502. The top surface 501 of the drawer 102 may face substantially upwards towards the top of the inhaler with respect to the longitudinal axis 106 and the bottom surface of the inhalation chimney 210 may face substantially downwards towards the bottom of the inhaler with respect to the longitudinal axis 106.

The top surface 501 may be curved in a convex manner and the bottom surface 502 may be curved in a concave manner corresponding to the curve of the top surface 501.

The protruding rib 401 may also be curved in the same manner as the top surface 501 and the bottom surface 502. In such an embodiment, a curve of the bottom surface of the protruding rib 401 may substantially match the curve of the bottom surface 502 of the inhalation chimney 210 and the curve of the top surface 501 of the drawer 102.

FIGS. 5A-B show a protruding rib 401 in which the second section is not angled upwards away from the perpendicular and instead matches the first section, such that the bottom surface of the protruding rib 401 comprises a single consistent curve. In such an embodiment, the guide post 219 may push the inhalation chimney 210 upwards by interacting with an edge of the protruding rib 401 and then sliding along the bottom surface of the protruding rib 401 towards the open position.

As can be seen in FIG. 5A, as the drawer 102 moves towards the closed position, the guide post 219 pushes the sealing ramp 404 downwards as it slides along the top surface 405 of the sealing ramp 404. This brings the top surface 501 of the drawer 102 and the bottom surface 502 of the inhalation chimney 210 closer together.

When the drawer 102 is in the closed position, the two surfaces may be brought into contact, or a small gap may remain between them. FIG. 5B shows a small gap remaining between the top surface 501 and the bottom surface 502. As a user inhales through the mouthpiece of the inhaler, the negative pressure caused by the inhalation may cause the spin chamber 103 to move upwards slightly such that the top surface 501 and bottom surface 502 are in direct contact with each other. In this way, a seal may be formed between the two surfaces.

Figure 6:
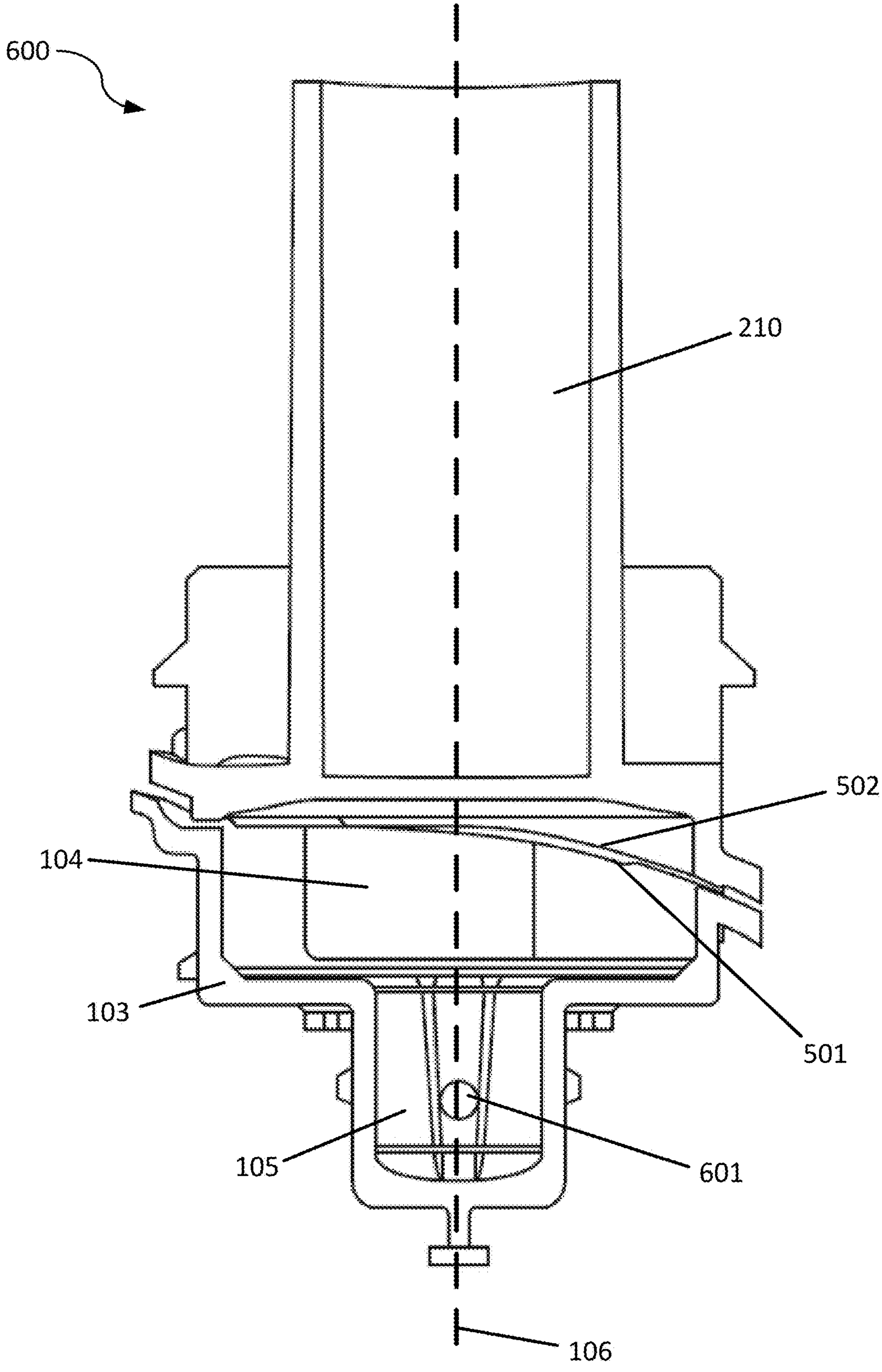
FIG. 6 shows a cross-sectional side view of the chimney and the drawer being held together in accordance with the present disclosure.

FIG. 6 shows a cross-sectional side view 600 of the inhalation chimney 210 and the spin chamber 103 of an inhaler being held together. The inhaler may the inhaler 100, 200, 300 or 400 from previous Figures.

When the drawer is in the closed position, the inhalation chimney 210 is positioned directly above the spin chamber 103 with respect to the longitudinal axis 106. As has been described, the spin chamber 103 may comprise a top surface 501 facing upwards with respect to the longitudinal axis 106. The top surface 501 may also be described as a top surface of the drawer, since the spin chamber 103 is located at the top of the drawer. The top surface 501 of the spin chamber 103 may be curved in a convex manner, as can be seen in FIG. 6.

As has also been described, the inhalation chimney 210 may comprise a bottom surface 502 facing downwards with respect to the longitudinal axis 106. The bottom surface 502 may be curved in concave manner corresponding to the curve of the top surface 501 of the spin chamber 103.

The spin chamber 103 may also comprise a pair of small apertures 601, through which the needles of the perforating means may pass into the secondary recess 105 during drawer closure in order to perforate a capsule placed in the secondary recess 105.

The top surface 501 and the bottom surface 502 are configured to be held together during inhalation, in order to define a chamber within which air can mix with the contents of a capsule inserted into the inhaler. This chamber may comprise the primary recess 104, the secondary recess 105 and a volume defined by the inhalation chimney 210. The curves of the two surfaces correspond to one another so that the spin chamber 103 and the inhalation chimney 210 may enclose the chamber.

When the drawer is in the closed position, the inhalation chimney 210 has been pulled downwards with respect to the longitudinal axis 106, as has been described. There may still be a small gap present between the top surface 501 and the bottom surface 502. As a user inhales through the mouthpiece of the inhaler, the negative pressure caused by the inhalation may cause the spin chamber 103 to move upwards slightly with respect to the longitudinal axis 106 such that the top surface 501 and bottom surface 502 are in direct contact with each other. In this way, a seal may be formed between the two surfaces.

As has been described with reference to FIG. 2, the drawer 102 is configured to rotate about an axle coupled to the main body 101 (such as a hinge mechanism), such that the drawer 102 can rotate relative to the main body 101 to move between the open position and the closed position, and wherein the clearance between the drawer 102 and the axle is such that the drawer 102 can move upwards with respect to the longitudinal axis 106 and relative to the main body 101 when the inhaler is used. It should be appreciated that only a small amount of movement is enabled, since too large a clearance could affect the structural integrity of the inhaler.

Figure 7A:
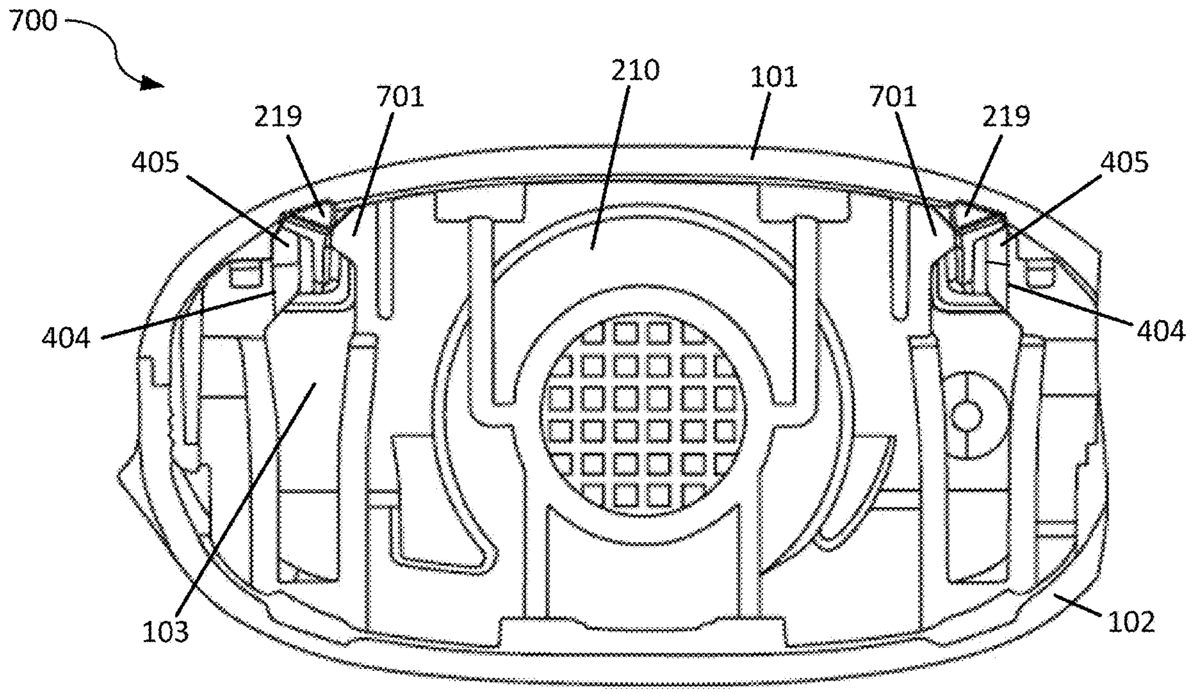
FIG. 7A shows a top view of a chimney shuttling mechanism of an inhaler when the drawer is in a closed position in accordance with the present disclosure.
Figure 7B:
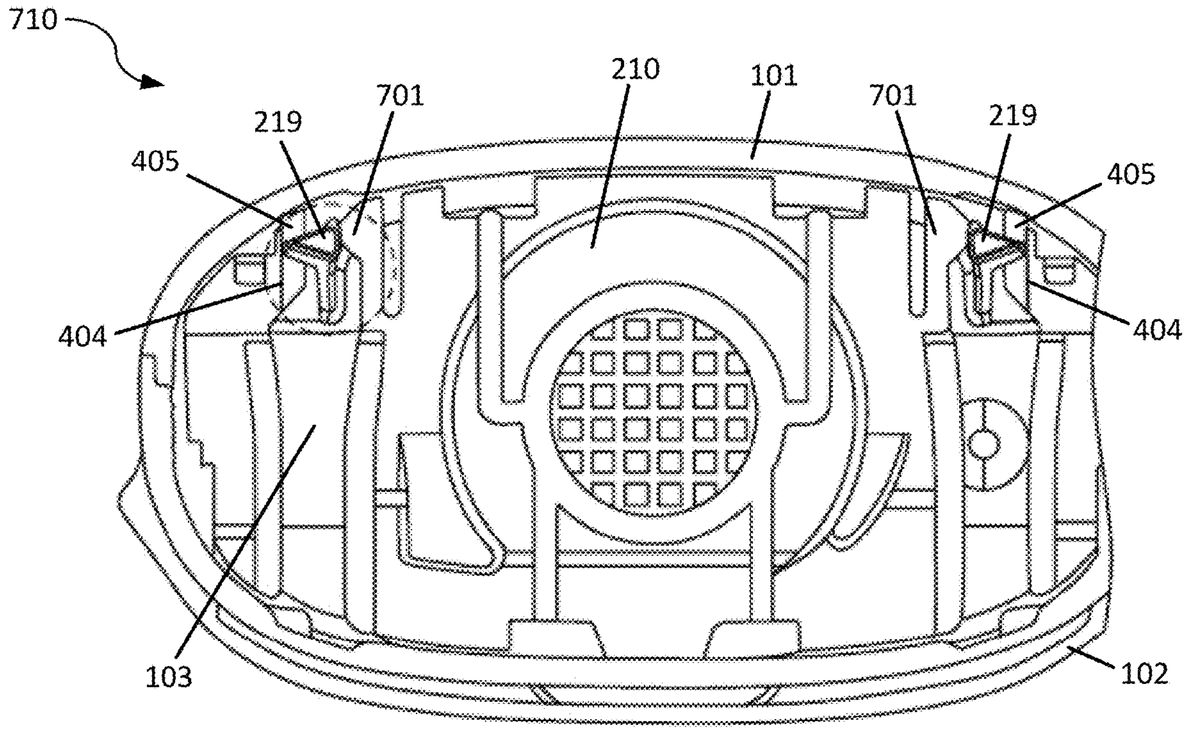
FIG. 7B shows a top view of a chimney shuttling mechanism of an inhaler when the drawer is beginning to move from a closed position towards an open position in accordance with the present disclosure.
Figure 7C:
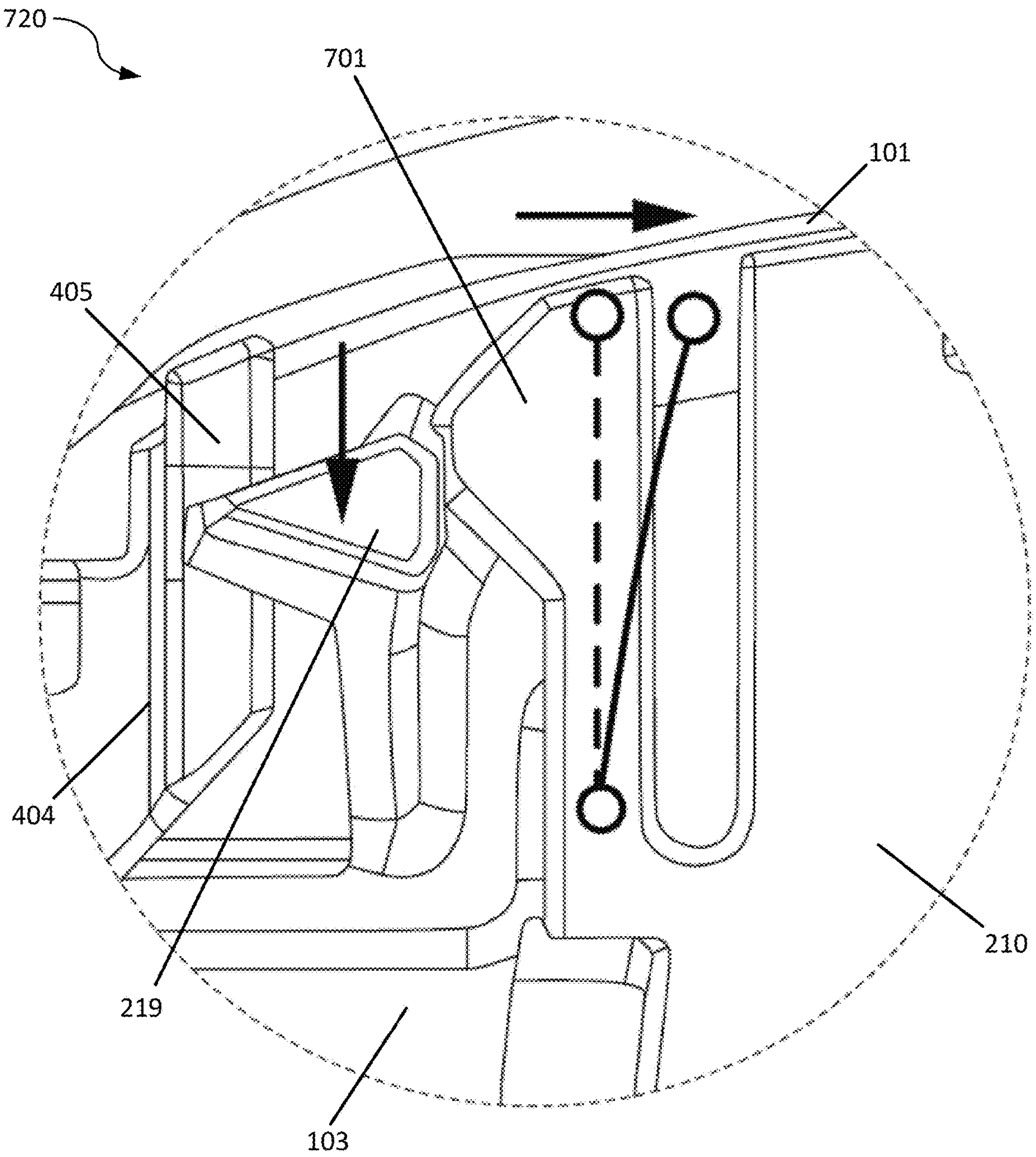
FIG. 7C shows an enlarged view of the chimney shuttling mechanism of FIG. 7B in accordance with the present disclosure.

FIGS. 7A-C show top views of a chimney shuttling mechanism of an inhaler, such as the chimney shuttling mechanism described with reference to FIGS. 4A-C and 5A-B. The inhaler may be the inhaler 100, 200, 300 or 400 from previous Figures. Specifically, FIG. 7A shows a top view 700 of a chimney shuttling mechanism when the drawer 102 is in a closed position, FIG. 7B shows a top view 710 of the same chimney shuttling mechanism when the drawer 102 is beginning to move from the closed position towards an open position, and FIG. 7C shows an enlarged view 720 of the same chimney shuttling mechanism at the same position as shown in FIG. 7B.

The features of the chimney shuttling mechanism have already been described with reference to FIGS. 4A-C and 5A-B.

The inhalation chimney 210 may also comprise at least one drawer retention clip 701. The at least one drawer retention clip 701 may be positioned at a side of the inhalation chimney 210 proximate to the rear casing of the main body 101 of the inhaler. FIGS. 7A-B show an embodiment in which the at least one drawer retention clip 701 comprises two drawer retention clips 701, each at opposing ends of the inhalation chimney 210.

The drawer retention clips 701 are configured to lock on to the guide posts 219 when the drawer 102 is in the closed position, thereby creating a retention force configured to hold the drawer 102 in the closed position. This prevents the drawer 102 from inadvertently opening during inhalation. In this embodiment, each of the two drawer retention clips 701 locks on to a different one of the two guide posts 219.

FIGS. 7B-C show the chimney shuttling mechanism as the drawer 102 is moved away from the closed position towards the open position. As the drawer 102 is pulled outwards, the guide posts 219 push the drawer retention clips 701 inwards towards the centre of the inhaler, so that the guide posts 219 may then move along with the rest of the drawer 102. Once the guide posts 219 have moved a sufficient distance away from the drawer retention clips 701, the drawer retention clips 701 may move back outwards to their normal resting position.

Various embodiments of the present disclosure include one or more of the following items:

1. An inhaler comprising: a main body comprising an inhalation chimney and a mouthpiece, the inhalation chimney comprising a bottom surface; and a drawer for receiving a capsule, the drawer comprising a top surface and configured to open out of and close into the main body; wherein the drawer is configured to move into the main body from an open position to a closed position, or out of the main body from the closed position to the open position, such that the movement of the drawer causes the inhalation chimney to move with respect to the mouthpiece; and wherein when the drawer is in the closed position, the top surface of the drawer and the bottom surface of the inhalation chimney are held together.

2. The inhaler of item 1, wherein the inhaler has a longitudinal axis extending from a top of the inhaler proximate to the mouthpiece, through the inhalation chimney and the drawer, to a bottom of the inhaler, wherein the drawer is positioned below the inhalation chimney with respect to the longitudinal axis, and wherein the inhalation chimney is configured to move along the longitudinal axis with respect to the mouthpiece as the drawer moves between the open position and the closed position.

3. The inhaler of item 2, wherein the inhalation chimney is raised with respect to the mouthpiece when the drawer is in the open position, and wherein a top surface of the inhalation chimney is level with a top surface of the mouthpiece when the drawer is in the closed position.

4. The inhaler of items 2 or 3, wherein the drawer comprises at least one guide post and the inhalation chimney comprises at least one protruding rib, the at least one protruding rib comprising a bottom surface facing down towards the bottom of the inhaler with respect to the longitudinal axis, wherein the at least one guide post is configured to slide along the bottom surface of the at least one protruding rib as the drawer moves between the open position and the closed position.

5. The inhaler of item 4, wherein the at least one guide post is configured to slide along the bottom surface of the at least one protruding rib as the drawer moves out of the main body from the closed position toward the open position, thereby causing the inhalation chimney to move upward.

6. The inhaler of items 4 or 5, wherein the protruding rib comprises a first section and a second section, wherein the first section is substantially perpendicular to the longitudinal axis and a bottom surface of the first section is curved in a concave manner.

7. The inhaler of item 6, wherein the second section is angled upward away from an perpendicular axis defined by the first section of the protruding rib.

8. The inhaler of items 6 or 7, wherein as the drawer moves into the main body from the open position towards the closed position, the at least one guide post is configured to slide along the bottom surface of the first section; and as the drawer moves out of the main body from the closed position towards the open position, the at least one guide post is configured to slide along the bottom surface of the second section, thereby causing the inhalation chimney to move upward, and then, the at least one guide post slides along the bottom surface of the first section.

9. The inhaler of any of items 4 to 8, wherein the inhalation chimney further comprises at least one sealing ramp configured to receive the at least one guide post, the at least one sealing ramp having a top surface facing up towards the top of the inhaler with respect to the longitudinal axis, wherein the at least one guide post is configured to slide along the top surface of the at least one sealing ramp as the drawer moves between the open position and the closed position.

10. The inhaler of item 9, wherein moving the drawer into the main body from the open position towards the closed position causes the at least one guide post to slide along the top surface of the at least one sealing ramp, thereby causing the inhalation chimney to move downwards with respect to the longitudinal axis.

11. The inhaler of items 9 or 10, wherein the inhalation chimney further comprises at least one drawer retention clip configured to lock on to the at least one guide post when the drawer is in the closed position, thereby creating a retention force configured to hold the drawer in a closed position.

12. The inhaler of any of items 9 to 11, wherein the drawer further comprises a front bridge and the inhalation chimney further comprises a front post, the front post configured to lock on to the front bridge when the drawer is in the closed position.

13. The inhaler of any of items 4 to 12, wherein the at least one guide post comprises two guide posts on opposing sides of the drawer.

14. The inhaler of any of item 13, wherein the at least one protruding rib comprises two protruding ribs on opposing sides of the inhalation chimney, wherein a first of the two protruding ribs is configured to interact with a first of the two guide posts and a second of the two protruding ribs is configured to interact with a second of the two guide posts.

15. The inhaler of any of items 9 to 14, wherein: the top surface of the drawer faces the top of the inhaler with respect to the longitudinal axis and is curved in a convex manner; and the bottom surface of the inhalation chimney faces the bottom of the inhaler with respect to the longitudinal axis and is curved in a concave manner corresponding to the curve of the top surface of the drawer.

16. The inhaler of item 15, wherein as the at least one guide post is configured to pass over the top surface of the at least one sealing ramp as the inhalation chimney is pulled towards the drawer.

17. The inhaler of item 16, wherein the inhaler is configured to create a negative pressure such that a seal is formed between the top surface of the drawer and the bottom surface of the inhalation chimney.

18. The inhaler of item 17, wherein the drawer is configured to move upward with respect to the longitudinal axis when the inhaler is used.

19. The inhaler of item 18, wherein the drawer is configured to rotate about an axle coupled to the main body, such that the drawer can rotate relative to the main body to move between the open position and the closed position, and wherein a clearance defined between the drawer and the axle is such that the drawer is configured to move upward with respect to the longitudinal axis and relative to the main body when the inhaler is used.

20. The inhaler of any of items 4 to 19, wherein the at least one guide post is configured to prevent the drawer from opening beyond a predetermined point.

It will be appreciated from the discussion above that the embodiments shown in the Figures are merely exemplary, and include features which may be generalized, removed or replaced as described herein and as set out in the claims.

Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the disclosure, which is defined in the accompanying claims.

Where ranges are recited herein these are to be understood as disclosures of the limits of said range and any intermediate values between the two limits.

With reference to the drawings in general, it will be appreciated that schematic functional block diagrams are used to indicate functionality of systems and apparatus described herein. It will be appreciated however that the functionality need not be divided in this way and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

Method embodiments may be implemented using the apparatus described herein.

The above embodiments are to be understood as illustrative examples. Further embodiments are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the disclosure, which is defined in the accompanying claims.

These claims are to be interpreted with due regard for equivalents.

The invention claimed is:

1. An inhaler comprising:
- a main body comprising an inhalation chimney and a mouthpiece, the inhalation chimney comprising a bottom surface; and
- a drawer for receiving a capsule, the drawer comprising a top surface and configured to open out of and close into the main body;
- wherein the drawer is configured to move into the main body from an open position to a closed position, or out of the main body from the closed position to the open position, such that the movement of the drawer causes the inhalation chimney to move with respect to the mouthpiece;
- and wherein when the drawer is in the closed position, the top surface of the drawer and the bottom surface of the inhalation chimney are held together.

2. The inhaler of claim 1, wherein the inhaler has a longitudinal axis extending from a top of the inhaler proximate to the mouthpiece, through the inhalation chimney and the drawer, to a bottom of the inhaler, wherein the drawer is positioned below the inhalation chimney with respect to the longitudinal axis, and wherein the inhalation chimney is configured to move along the longitudinal axis with respect to the mouthpiece as the drawer moves between the open position and the closed position.

3. The inhaler of claim 2, wherein the inhalation chimney is raised with respect to the mouthpiece when the drawer is in the open position, and wherein a top surface of the inhalation chimney is level with a top surface of the mouthpiece when the drawer is in the closed position.

4. The inhaler of claim 2, wherein the drawer comprises at least one guide post and the inhalation chimney comprises at least one protruding rib, the at least one protruding rib comprising a bottom surface facing down towards the bottom of the inhaler with respect to the longitudinal axis, wherein the at least one guide post is configured to slide along the bottom surface of the at least one protruding rib as the drawer moves between the open position and the closed position.

5. The inhaler of claim 4, wherein the at least one guide post is configured to slide along the bottom surface of the at least one protruding rib as the drawer moves out of the main body from the closed position toward the open position, thereby causing the inhalation chimney to move upward.

6. The inhaler of claim 4, wherein the protruding rib comprises a first section and a second section, wherein the first section is substantially perpendicular to the longitudinal axis and a bottom surface of the first section is curved in a concave manner.

7. The inhaler of claim 6, wherein the second section is angled upward away from an perpendicular axis defined by the first section of the protruding rib.

8. The inhaler of claim 6, wherein:
- as the drawer moves into the main body from the open position towards the closed position, the at least one guide post is configured to slide along the bottom surface of the first section; and
- as the drawer moves out of the main body from the closed position towards the open position, the at least one guide post is configured to slide along the bottom surface of the second section, thereby causing the inhalation chimney to move upward, and then, the at least one guide post slides along the bottom surface of the first section.

9. The inhaler of claim 4, wherein the inhalation chimney further comprises at least one sealing ramp configured to receive the at least one guide post, the at least one sealing ramp having a top surface facing up towards the top of the inhaler with respect to the longitudinal axis, wherein the at least one guide post is configured to slide along the top surface of the at least one sealing ramp as the drawer moves between the open position and the closed position.

10. The inhaler of claim 9, wherein moving the drawer into the main body from the open position towards the closed position causes the at least one guide post to slide along the top surface of the at least one sealing ramp, thereby causing the inhalation chimney to move downwards with respect to the longitudinal axis.

11. The inhaler of claim 9, wherein the inhalation chimney further comprises at least one drawer retention clip configured to lock on to the at least one guide post when the drawer is in the closed position, thereby creating a retention force configured to hold the drawer in a closed position.

12. The inhaler of claim 9, wherein the drawer further comprises a front bridge and the inhalation chimney further comprises a front post, the front post configured to lock on to the front bridge when the drawer is in the closed position.

13. The inhaler of claim 9, wherein:

the top surface of the drawer faces the top of the inhaler with respect to the longitudinal axis and is curved in a convex manner; and the bottom surface of the inhalation chimney faces the bottom of the inhaler with respect to the longitudinal axis and is curved in a concave manner corresponding to the curve of the top surface of the drawer.

14. The inhaler of claim 13, wherein as the at least one guide post is configured to pass over the top surface of the at least one sealing ramp as the inhalation chimney is pulled towards the drawer.

15. The inhaler of claim 14, wherein the inhaler is configured to create a negative pressure such that a seal is formed between the top surface of the drawer and the bottom surface of the inhalation chimney.

16. The inhaler of claim 15, wherein the drawer is configured to move upward with respect to the longitudinal axis when the inhaler is used.

17. The inhaler of claim 16, wherein the drawer is configured to rotate about an axle coupled to the main body, such that the drawer can rotate relative to the main body to move between the open position and the closed position, and wherein a clearance defined between the drawer and the axle is such that the drawer is configured to move upward with respect to the longitudinal axis and relative to the main body when the inhaler is used.

18. The inhaler of claim 4, wherein the at least one guide post comprises two guide posts on opposing sides of the drawer.

19. The inhaler of claim 18, wherein the at least one protruding rib comprises two protruding ribs on opposing sides of the inhalation chimney, wherein a first of the two protruding ribs is configured to interact with a first of the two guide posts and a second of the two protruding ribs is configured to interact with a second of the two guide posts.

20. The inhaler of claim 4, wherein the at least one guide post is configured to prevent the drawer from opening beyond a predetermined point.

* * * * *